(12) United States Patent
Chen et al.

(10) Patent No.: US 11,134,926 B2
(45) Date of Patent: Oct. 5, 2021

(54) SPIRAL SOFT TISSUE BIOPSY NEEDLE

(71) Applicants: Shihui Chen, Beijing (CN); Xinru Du, Beijing (CN)

(72) Inventors: Shihui Chen, Beijing (CN); Xinru Du, Beijing (CN)

( * ) Notice: Subject to any disclaimer, the term of this patent is extended or adjusted under 35 U.S.C. 154(b) by 507 days.

(21) Appl. No.: 15/997,694

(22) Filed: Jun. 5, 2018

(65) Prior Publication Data
US 2018/0280003 A1    Oct. 4, 2018

Related U.S. Application Data

(63) Continuation of application No. PCT/CN2016/099430, filed on Sep. 20, 2016.

(30) Foreign Application Priority Data

Aug. 31, 2016 (CN) .......................... 201610792736.6

(51) Int. Cl.
*A61B 10/02* (2006.01)
*A61B 10/04* (2006.01)

(52) U.S. Cl.
CPC .......... *A61B 10/0266* (2013.01); *A61B 10/02* (2013.01); *A61B 10/04* (2013.01)

(58) Field of Classification Search
CPC ..... A61B 10/0266; A61B 10/02; A61B 10/04; A61B 10/0233; A61B 10/025; A61B 10/0096
See application file for complete search history.

(56) References Cited

U.S. PATENT DOCUMENTS

| | | | | |
|---|---|---|---|---|
| 5,709,697 A | * | 1/1998 | Ratcliff | A61B 10/0266 606/167 |
| 6,083,237 A | * | 7/2000 | Huitema | A61B 10/0233 600/567 |
| 7,008,381 B2 | * | 3/2006 | Janssens | A61B 10/0233 600/564 |
| 2004/0127814 A1 | * | 7/2004 | Negroni | A61B 10/025 600/567 |
| 2009/0018468 A1 | * | 1/2009 | Janssens | A61B 10/0266 600/567 |

\* cited by examiner

*Primary Examiner* — Devin B Henson
(74) *Attorney, Agent, or Firm* — Yong Chen

(57) ABSTRACT

Provided is a spiral soft tissue biopsy needle, comprising a puncture needle rod (1), a sampling needle rod (2), and a hand shank (3) for fixing the puncture needle rod (1) and the sampling needle rod (2), wherein the sampling needle rod (2) comprises a spiral needle rod (21) for fixing the sampling site and a cutting needle rod (22) for separating the sample from the sampling site, the spiral needle rod (21) has a hollow structure, the front end of the spiral needle rod (21) is provided with a spring spiral tube (211), and the front end of the cutting needle rod (22) is provided with a cutting edge (221). The spiral soft tissue biopsy needle of the present invention can improve the success rate of one-time sampling and achieve a multi-point sampling in different positions.

10 Claims, 17 Drawing Sheets

SPIRAL SOFT TISSUE BIOPSY NEEDLE

CROSS-REFERENCE TO RELATED APPLICATION

This application is a continuation of International Application No. PCT/CN2016/099430, filed Sep. 20, 2016, which claims priority to Chinese Patent Application No. 201610792736.6, filed Aug. 31, 2016. The disclosure of each of these prior-filed applications is incorporated herein by reference in its entirety.

TECHNICAL FIELD

The present invention relates to the field of medical devices, and more particularly, to a spiral soft tissue biopsy needle for a soft tissue sampling or small tumor resection.

BACKGROUND ART

Puncture biopsy, which is a medical diagnostic method often used for kidney, liver, lung, breast, thyroid, prostate, pancreas, testis, uterus, ovary, body surface and other organs, can be used for living tissue sampling and cell aspiration of pyramidal tumors and unknown tumors, etc. The commonly used biopsy needle has a small diameter for reduced trauma in the sampling operation, which is simple and can be carried out under local anesthesia in a clinic setting. The tissue damage and bleeding caused by such small diameter biopsy needle is rather minimal, and the sampling procedure is quite safe and has very low chance of infection.

There are primarily two types of currently available biopsy needles: gripping type and rotary cutting type. As shown in FIG. 1, the gripping type biopsy needle is equipped with a gripping head at the distal end of the needle. As shown in FIG. 2, when the gripping type biopsy needle takes a sample, the gripping head goes deep into the sampling site, the push-pull rod is pulled to close the gripping head to take out the sample. As shown in FIG. 3, the rotary cutting type biopsy needle is equipped with a rotary cutting edge at the distal end of the needle. As shown in FIG. 4, when the rotary cutting type biopsy needle takes a sample, the rotary cutting edge goes deep into the sampling site, and the sampling can be achieved by rotating the sampling tube, which removes the sample from the tissue and retains the removed sample in a groove of the rotary cutting edge. These two sampling methods have the following problems: (1) the amount of sample obtained cannot be precisely determined beforehand; (2) they cannot be used for multi-point continuous sampling; (3) they have rather low success rate when the sampling site is small or thin; (4) they cannot be used to take a sample from a site at a body cavity wall; (5) they cannot be used to take a sample from a site having a high degree of decay or high degree of fluidity.

Chinese Patent Application No. 201110462413.8 discloses a hole-wall type biopsy needle, which is formed by an anti-skidding handle, a needle body, a sampling ring, an annular groove and a needle tip, wherein the upper end of the needle body is provided with the rectangular-sheet-shaped anti-skidding handle which is bonded with the needle body into a whole, the side wall of the anti-skidding handle is provided with multiple convex strips, the lower end of the needle body is the needle tip. A circular sampling ring is provided above the needle tip and is integrated with the needle body. In the inner side wall of the sampling ring is provided with the an groove which has a V-shaped cross section, where the top angle is between 105° and 120°, and two annular inner walls of the V-shaped annular groove respectively form a cutting edge with each of two annular side walls of the sampling ring. This biopsy needle can take larger sample quantity and improve the sampling efficiency, but still fails to take samples in a quantitative manner or take multiple samples at multiple sites continuously.

Chinese Patent Application No. 201010214740.7 discloses a visceral layer biopsy needle, which comprises a needle tube and an inner sleeve internally sleeved in the needle tube. The inner surface of the needle tube and the outer surface of the inner sleeve are respectively provided with an internal thread and an external thread which are matched mutually. A piston and a piston rod connected with the piston are arranged in the inner sleeve. A through hole is formed in the wall of the inner sleeve along the axial direction. A sampling cutter control rod is arranged in the through hole. One end of the sampling cutter control rod, which is close to a needlepoint, is fixedly connected with a crescent sampling cutter. The piston mechanism of this disclosure can form a negative pressure to thereby adhere lesion tissues of the surface of a visceral layer and improve the sampling accuracy, but it still fails to realize the multi-point continuous sampling and fails to control the sampling quantity.

Chinese Patent Application No. 200810013943.2 discloses a multiple-spots biopsy needle, which consists of a casing and a needle core positioned in the casing and wherein: the inner part of the needle core is hollow and the outer surface of the needle core is provided with graduation marks and provided with a round cutter at fixed distance intervals. On the outer surface of the casing are provided with graduation marks, as well as an auto spring controlling the needle core. The auto spring is positioned within a spring jacket which is fixed with a handle. The device of this disclosure enables simultaneous multi-point sampling at different cutter positions, but the sampling quantity is small and quantitative sampling cannot be achieved, and the positions of the multi-point sampling are limited by the cutter position.

Chinese Patent Application No. 201510441591.0 discloses a replaceable core-taking biopsy needle, which includes an elongate tubular body comprising a lumen extending therethrough from a proximal open end to a distal open end of the body. The distal end includes first and second tip portions extending therefrom and radially opposing one another. The first tip portion has a length greater than that of the second tip portion, thereby resulting in an increased surface area of a curvilinear cutting edge extending from the first tip portion to the second tip portion. Each of the first and second tip portions defines a point configured to pierce the tissue to be sampled and further direct tissue towards the lumen of the body to be excised by the cutting edge upon contact therewith.

SUMMARY OF THE INVENTION

A first object of the present invention is to solve the problems in the prior art that currently available biopsy needles cannot achieve quantitative samplings during sampling, and one-time success rate of sampling is low.

A second object of the present invention is to solve the problems in the prior art that currently available biopsy needle cannot achieve multi-point continuous samplings or the success rate of sampling is low in a multi-point continuous sampling process.

A third object of the present invention is to solve the technical problem in the prior art that the success rate of sampling large samples is low.

A fourth object of the present invention is to solve the technical problem in the prior art that the tumor cannot be taken out as a whole.

In order to achieve the first and the second objects of the present invention, the present disclosure provides a spiral soft tissue biopsy needle comprising a puncture needle rod, a sampling needle rod, and a hand shank for fixing the puncture needle rod and the sampling needle rod; the sampling needle rod comprises a spiral needle rod for fixing the sampling site and a cutting needle rod for separating the sample from the sampling site, the spiral needle rod has a hollow structure, the cutting needle rod is arranged on the outer side of the spiral needle rod and the inner surface of the cutting needle rod is in close contact with the outer surface of the spiral needle rod, the front end of the spiral needle rod is provided with a spring spiral tube, and the front end of the cutting needle rod is provided with a cutting edge. The inner surface of the cutting needle rod is in close contact with the outer surface of the spiral needle rod so that the cutting edge can produce shearing effect with the thread of the spring spiral tube when cutting the samples to improve the efficiency and accuracy of the cutting of samples. The spring spiral tube can immobilize the sampling site and improve the success rate of one-time sampling, and the samples can be accommodated into the threads of the spiral tube and can coordinate with the cutting needle rod in the process of sampling, to improve the sampling efficiency and achieve a quantitative sampling, while increasing the length of the thread of the spring spiral tube can achieve a multi-point sampling in different positions on the same line.

As a preferred embodiment of the spiral soft tissue biopsy needle according to the present invention, the front end of the spring spiral tube is provided with a spiral cutting edge. The spiral cutting edge remains inactive during the rotational advancement of the spiral needle to the sampling site. After the cutting of the sample has been completed by the cutting edge, the spiral needle rod can be rotated to drive the spring spiral tube to rotate. At this time, the spiral cutting edge can cut off the front end of the samples during the rotation, thereby improving the accuracy of sampling. This improvement effect is more obvious when the sample to be taken has a large diameter.

As a preferred embodiment of the spiral soft tissue biopsy needle according to the present invention, the last thread or the last two threads on the front end of the spring spiral tube has a diameter less than the diameter of the other threads of the spring spiral tube. The thread on the front end of the spring spiral tube connects with the spiral edge and has a slightly smaller diameter, and thus the cross-sectional area of the front end of the samples can be reduced and the sampling accuracy can be improved.

As a preferred embodiment of the spiral soft tissue biopsy needle according to the present invention, the hand shank comprises a handle which is provided in the middle with a through hole for the puncture needle rod or sampling needle rod to go through, the front end of the handle is provided with a hollow sampling outer tube for directional movement of the puncture needle rod or the sampling needle rod, the outer side of the sampling outer tube is provided with a first positioning block, the rear end of the handle is provided with a fixed groove for fixing the puncture needle rod or the sampling needle rod, and the fixed groove is provided with two steps for fixing the spiral needle rod and the cutting needle rod, respectively. The first positioning block can position the puncture site and can realize the fixing of the sampling needle rod in combination with the fixed groove, thus providing a foundation for accurate positioning and quantitative sampling.

As a preferred embodiment of the spiral soft tissue biopsy needle according to the present invention, the puncture needle rod further includes a puncture needle and a puncture needle rod fixture attached to the tail of the puncture needle, the puncture needle has an outer diameter equal to the inner diameter of the sampling outer tube.

As a preferred embodiment of the spiral soft tissue biopsy needle according to the present invention, the spiral needle rod further comprises a spiral needle rod outer tube fixedly connected to the tail end of the spring spiral tube, the spiral needle rod outer tube has a hollow structure and has an outer diameter smaller than or equal to the inner diameter of the sampling outer tube, the outer diameter of the spiral needle rod outer tube is equal to the outer diameter of the spring spiral tube tail or the inner diameter of the spiral needle rod outer tube is equal to the inner diameter of the spring spiral tube tail, the tail end of the spiral needle rod outer tube is provided with a spiral needle rod fixture for fixing the spiral needle rod outer tube to the fixed groove.

As a preferred embodiment of the spiral soft tissue biopsy needle according to the present invention, the cutting needle rod comprises an cutting needle rod outer tube with a hollow structure which has an outer diameter equal to or smaller than the inner diameter of the sampling outer tube, a cutting edge is arranged on the front end of the cutting needle rod outer tube, and a cutting needle rod fixture for fixing the cutting needle rod outer tube to the fixed groove is provided at the tail end of the cutting needle rod outer tube.

As a preferred embodiment of the spiral soft tissue biopsy needle according to the present invention, the cutting edge has at least two teeth in a triangular or undulating shape in close contact with the outer surface of the spring spiral tube. The multi-group cutting edge teeth can improve the cutting efficiency and shorten the cutting time. The triangular or undulating cutting edge teeth helps to cut the samples effectively, and the teeth in close contact with the outer surface of the spring spiral tube enable the formation of shear force between the teeth and the spiral tube threads and thus improve the cutting efficiency.

As a preferred embodiment of the spiral soft tissue biopsy needle according to the present invention, the other end of the spiral needle rod is provided with a rotary rod for rotating the spiral needle rod or cutting needle rod, and the rotary rod and the spiral needle rod fixture are connected through threads. The rotary rod can rotate the spiral needle rod to the sampling site, and can also drive the cutting needle rod to cut the samples.

As a preferred embodiment of the spiral soft tissue biopsy needle according to the present invention, the fixed groove is provided with a fixed module for positioning the spiral needle rod and the cutting needle rod, where the fixed module has a U-shaped cross section and is provided in the middle with a first through hole for the thread to go through, the spiral needle rod fixture and the cutting needle rod fixture are arranged in the cavity composed of the fixed groove and the fixed module, the outer side of the thread on the front end of the rotary rod is provided with a second positioning block for positioning the spiral needle rod and the cutting needle rod. The fixed module is able to position the spring spiral tube and enable quantitative sampling at a specific position, as well as a multi-point sampling in the same line at once.

As a preferred embodiment of the spiral soft tissue biopsy needle according to the present invention, the spiral soft tissue biopsy needle further comprises a push rod for pushing an absorbent gelatin into the sampling site, where the push rod comprises a round rod, and the tail of the round rod is provided with a push rod fixture for positioning the push rod. The push rod is able to push the absorbent gelatin for healing the wound into the sampling site and promote the healing of the wound.

As a preferred embodiment of the spiral soft tissue biopsy needle according to the present invention, it further comprises a vacuum device, a second through hole connecting with the hollow part of the sampling outer tube is arranged at the upper end of the handle, a first joint is arranged on the outer side of the handle at the upper end of the second through hole, a third through hole connecting with the rear end of the sampling outer tube is arranged in the middle part of the rotary rod, and a second joint is provided at the outer end of the rotary rod at the outer end of the third through hole, and the vacuum device is connected with the first joint or the second joint. In the process of puncture, the vacuum device is connected with the first joint, which allows the timely discharge of the blood generated in the puncture process, and timely eliminate liquid that interferes with the sampling site (such as suppuration after festering), and when the samples of the sampling site have good fluidity, the sampling can be achieved by directly sucking the samples out of the second joint; in the process of positioning and cutting, the vacuum device is connected with the second joint to form a negative pressure in the spiral needle rod outer tube or the cutting needle rod outer tube, which helps cutting of the samples and the separation of the samples from the remaining tissues of the sampling site and thus can improve the accuracy of sampling.

As a preferred embodiment of the spiral soft tissue biopsy needle according to the present invention, the spiral soft tissue biopsy needle further includes a sampling device, comprising an upper sampling shell and a lower sampling shell, the upper sampling shell is provided with an upper sampling groove inside, the lower sampling shell is provided with a lower sampling groove inside, the upper sampling groove corresponds to the lower sampling groove in shape and the shape after their closure coincides with the thread shape of the spring spiral tube. After the sampling is finished, the spring spiral tube containing the samples is placed into the sampling device, the sampling device is closed, the spring spiral tube is taken out by rotation in a reverse direction, the samples will be left behind in the sampling device, and then the sampling device is opened to give the final samples.

To achieve the third object of the present invention, there is provided a spiral soft tissue biopsy needle comprising a puncture needle rod, a sampling needle rod, and a hand shank for fixing the puncture needle rod and the sampling needle rod; and the sampling needle rod comprises a spiral needle rod for fixing the sampling site and a cutting needle rod for separating the sample from the sampling site, the spiral needle rod has a hollow structure, the cutting needle rod is arranged on the outer side of the spiral needle rod and the outer surface of the cutting needle rod is in close contact with the inner surface of the spiral needle rod, the front end of the spiral needle rod is provided with a spring spiral tube, and the front end of the cutting needle rod is provided with a cutting edge. The outer surface of the cutting needle rod is in close contact with the inner surface of the spiral needle rod so that the cutting edge can form shear force with the threads of the spring spiral tube when cutting the samples to improve the efficiency and accuracy of the cutting of samples. The spring spiral tube can fix the sampling site and improve the success rate of one-time sampling. The sample can be retained in the threads of the spiral tube, which together with the cutting needle rod in the course of sampling, improve the sampling efficiency and achieve quantitative sampling, while increasing the length of the spring spiral tube can enable multi-point sampling in different positions on a same straight line.

As a preferred embodiment of the spiral soft tissue biopsy needle according to the present invention, the front end of the spring spiral tube is provided with a spiral cutting edge. The spiral cutting edge remain inactive when the spiral needle rod is being rotated to the sampling site. After the cutting edge finishes the cutting of the samples, the spiral needle rod is rotated to drive the spring spiral tube to rotate. The spiral cutting edge can cut off the front end of the samples during the rotation, thereby improving the accuracy of the sampling. This effect is more obvious when the samples have a great diameter.

As a preferred embodiment of the spiral soft tissue biopsy needle according to the present invention, the hand shank comprises a handle which is provided in the middle with a through hole for the puncture needle rod or sampling needle rod to go through, the front end of the handle is provided with a hollow sampling outer tube for directional movement of the puncture needle rod or the sampling needle rod, the outer side of the sampling outer tube is provided with a first positioning block, the rear end of the handle is provided with a fixed groove for fixing the puncture needle rod or the sampling needle rod, and the fixed groove is provided with two steps for fixing the spiral needle rod and the cutting needle rod, respectively. The first positioning block can position the puncture site and can realize the fixing of the sampling needle rod in combination with the fixed groove, thus providing a basis for the quantitative sampling at specific positions.

As a preferred embodiment of the spiral soft tissue biopsy needle according to the present invention, the puncture needle rod further includes a puncture needle and a puncture needle rod fixture attached to the tail of the puncture needle, the puncture needle has an outer diameter equal to the inner diameter of the sampling outer tube.

As a preferred embodiment of the spiral soft tissue biopsy needle according to the present invention, the spiral needle rod further comprises a spiral needle rod outer tube fixedly connected to the tail end of the spring spiral tube, the spiral needle rod outer tube has a hollow structure and has an outer diameter smaller than or equal to the inner diameter of the sampling outer tube, the outer diameter of the spiral needle rod outer tube is equal to the outer diameter of the spring spiral tube tail or the inner diameter of the spiral needle rod outer tube is equal to the inner diameter of the spring spiral tube tail, the tail end of the spiral needle rod outer tube is provided with a spiral needle rod fixture for fixing the spiral needle rod outer tube to the fixed groove.

As a preferred embodiment of the spiral soft tissue biopsy needle according to the present invention, the cutting needle rod comprises an cutting needle rod outer tube with a hollow structure which has an outer diameter equal to or smaller than the inner diameter of the sampling outer tube, a cutting edge is arranged on the front end of the cutting needle rod outer tube, and a cutting needle rod fixture for fixing the cutting needle rod outer tube to the fixed groove is provided at the tail end of the cutting needle rod outer tube.

As a preferred embodiment of the spiral soft tissue biopsy needle according to the present invention, the cutting edge has at least two teeth in a triangular or undulating shape in close contact with the outer surface of the spring spiral tube.

The multi-group cutting edge teeth can improve the cutting efficiency and shorten the cutting time. The triangular or undulating cutting edge teeth help to cut the samples effectively, and the teeth in close contact with the outer surface of the spring spiral tube enable the formation of shear force between the teeth and the spiral tube thread and thus improve the cutting efficiency.

As a preferred embodiment of the spiral soft tissue biopsy needle according to the present invention, the other end of the spiral needle rod is provided with a rotary rod for rotating the spiral needle rod or cutting needle rod, and the rotary rod and the spiral needle rod fixture are connected through a thread. The rotary rod can rotate the spiral needle rod to the sampling site, and can also drive the cutting needle rod to cut the sample.

As a preferred embodiment of the spiral soft tissue biopsy needle according to the present invention, the fixed groove is provided with a fixed module for positioning the spiral needle rod and the cutting needle rod, where the fixed module has a U-shaped cross section and is provided in the middle with a first through hole for the thread to go through, the spiral needle rod fixture and the cutting needle rod fixture are arranged in the cavity formed by the fixed groove and the fixed module, where the outer side of the thread on the front end of the rotary rod is provided with a second positioning block for positioning the spiral needle rod and the cutting needle rod. The fixed module is able to position the spring spiral tube, and enable quantitative sampling at specific positions, as well as a multi-point sampling in the same straight line all at once.

As a preferred embodiment of the spiral soft tissue biopsy needle according to the present invention, the spiral soft tissue biopsy needle further comprises a push rod for pushing the absorbent gelatin into the sampling site, the push rod comprises a round rod, the tail of the round rod is provided with a push rod fixture for positioning the push rod. The push rod is able to push the absorbent gelatin for healing the patient's wound into the sampling site and helps the patient's wound heal.

As a preferred embodiment of the spiral soft tissue biopsy needle according to the present invention, it further comprises a vacuum device, a second through hole connecting with the hollow part of the sampling outer tube is arranged at the upper end of the handle, a first joint is arranged on the outer side of the handle at the upper end of the second through hole, a third through hole connecting with the rear end of the sampling outer tube is arranged in the middle part of the rotary rod, and a second joint is provided at the outer end of the rotary rod at the outer end of the third through hole, and the vacuum device is connected with the first joint or the second joint. In the process of puncture, the vacuum device connected with the first joint can timely discharge the blood generated, and eliminate the liquid that interferes with the sampling site (such as suppuration after festering), and when the samples of the sampling site have good fluidity, the sampling can be achieved by directly sucking the samples out of the second joint; in the process of positioning and cutting, the vacuum device is connected with the second joint to form a negative pressure in the spiral needle rod outer tube or the cutting needle rod outer tube, which helps to the cutting of the sample and the separation of the samples from the remaining tissues of the sampling site and thus can improve the accuracy of sampling.

As a preferred embodiment of the spiral soft tissue biopsy needle according to the present invention, the spiral soft tissue biopsy needle further includes a sampling device comprising an upper sampling shell and a lower sampling shell, the upper sampling shell is provided with an upper sampling groove inside, the lower sampling shell is provided with a lower sampling groove inside, the upper sampling groove corresponds to the lower sampling groove in shape and the shape after their closure coincides with the thread shape of the spring spiral tube. After the sampling is finished, the spring spiral tube containing the sample is put into the sampling device, the sampling device is closed, the spring spiral tube is taken out by rotation in a reverse direction, the samples will be left behind in the sampling device, and then the sampling device is opened to give the final samples.

A method of using the spiral soft tissue biopsy needle according to the invention comprises the following steps:

S1, adjusting the sampling length of the sampling needle rod according to the sampling requirements;

S2, fixing the puncture needle rod on the hand shank and putting the hand shank to puncture to the sampling site;

S3, removing the puncture needle rod from the hand shank and fixing the sampling needle rod on the hand shank;

S4, taking samples according to the sampling length adjusted in S1;

S5, taking out both the samples and the sampling needle rod from the hand shank at the same time;

S6, separating the samples from the sampling needle rod.

In a preferred embodiment, a method of using the spiral soft tissue biopsy needle according to the invention further comprises the following step:

S7, pushing an absorbent gelatin into the sampling site through a push rod.

In the method of using the spiral soft tissue biopsy needle according to the invention, as a preferred embodiment, the step S1 further comprises the following steps:

S11, connecting the spiral needle rod with the cutting needle rod and fixedly connecting the spiral needle rod fixture with the fixed module;

S12, connecting the fixed module with the hand shank fixedly;

S13, adjusting the sampling length by adjusting the length of the spring spiral rod extending out of the cutting needle rod.

In the method of using the spiral soft tissue biopsy needle according to the invention, as a preferred embodiment, the step S4 further comprises the following steps:

S41, rotating the spiral needle rod through the rotary rod into the sampling site for fixation of a sample;

S42, connecting the vacuum device with the second joint and performing vacuuming;

S43, rotating the cutting needle rod through the rotary rod to cut the side of the sample;

S44, rotating the spiral needle rod through the rotary rod to cut the bottom of the sample;

S45, completing the sampling after taking out the spiral needle rod and cutting needle rod.

In the method of using the spiral soft tissue biopsy needle according to the invention, as a preferred embodiment, the step S6 further comprises the following steps:

S61, opening the sampling device and placing the spring spiral tube on the lower sampling groove;

S62, closing the sampling device;

S63, rotating the spring spiral tube in a reverse direction to separate it from the sampling device;

S64, opening the sampling device and taking out the samples.

To achieve the forth object of the present invention, there is provided a spiral soft tissue biopsy needle comprising a puncture needle rod, a sampling needle rod, a hand shank for fixing the puncture needle rod and the sampling needle rod and an end cutter arranged on the outer side of the front end of the sampling needle rod, and the sampling needle rod comprises a spiral needle rod for fixing the sampling site and a cutting needle rod for separating the sample from the sampling site, the spiral needle rod has a hollow structure, wherein the cutting needle rod is arranged on the outer side of the spiral needle rod and the inner surface of the cutting needle rod is in close contact with the outer surface of the spiral needle rod, the front end of the spiral needle rod is provided with a spring spiral tube, and the front end of the cutting needle rod is provided with a cutting edge, an end cutter is arranged on the outer side of the cutting edge. The inner surface of the cutting needle rod is in close contact with the outer surface of the spiral needle rod so that the cutting edge can form shear force with the thread of the spring spiral tube when cutting the samples to improve the efficiency and accuracy of the cutting of sampling. The spring spiral tube can fix the sampling site and improve the success rate of one-time sampling, and the sample can be embedded in the thread of the spiral tube and can coordinate with the cutting needle rod in the course of sampling to improve the sampling efficiency and achieve a quantitative sampling, while increasing the length of the thread of the spring spiral tube can achieve a multi-point sampling in different positions on the same line. The end cutter can cut off the small tumor as a whole and take it out.

As a preferred embodiment of the spiral soft tissue biopsy needle according to the present invention, the front end of the spring spiral tube is provided with a spiral cutting edge. The spiral cutting edge remains inactive while the spiral needle rod is being rotated to the sampling site. After the cutting of the samples has been completed by the cutting edges, the spiral needle rod can be rotated to drive the spring spiral tube to rotate. At this time, the spiral cutting edge can cut off the front end of the samples during the rotation, thereby improving the accuracy of sampling. This improvement effect is more obvious when the sample to be taken has a large diameter.

As a preferred embodiment of the spiral soft tissue biopsy needle according to the present invention, the last thread or the last two threads on the front end of the spring spiral tube has a diameter less than the diameter of the other threads of the spring spiral tube. The thread on the front end of the spring spiral tube connects with the spiral edge and has a slightly smaller diameter, and thus the cross-sectional area of the front end of the samples can be reduced and the sampling accuracy can be improved.

As a preferred embodiment of the spiral soft tissue biopsy needle according to the present invention, the hand shank comprises a handle which is provided in the middle with a through hole for the puncture needle rod or sampling needle rod to go through, the front end of the handle is provided with a hollow sampling outer tube for directional movement of the puncture needle rod or the sampling needle rod, the outer side of the sampling outer tube is provided with a first positioning block, the rear end of the handle is provided with a fixed groove for fixing the puncture needle rod or the sampling needle rod, and the fixed groove is provided with two steps for fixing the spiral needle rod and the cutting needle rod, respectively. The first positioning block can position the puncture site and can realize the fixing of the sampling needle rod in combination with the fixed groove, thus providing a basis for the positioning quantitative sampling.

As a preferred embodiment of the spiral soft tissue biopsy needle according to the present invention, the puncture needle rod further includes a puncture needle and a puncture needle rod fixture attached to the tail of the puncture needle, the puncture needle has an outer diameter equal to the inner diameter of the sampling outer tube.

As a preferred embodiment of the spiral soft tissue biopsy needle according to the present invention, the spiral needle rod further comprises a spiral needle rod outer tube fixedly connected to the tail end of the spring spiral tube, the spiral needle rod outer tube has a hollow structure and has an outer diameter smaller than or equal to the inner diameter of the sampling outer tube, the outer diameter of the spiral needle rod outer tube is equal to the outer diameter of the spring spiral tube tail or the inner diameter of the spiral needle rod outer tube is equal to the inner diameter of the spring spiral tube tail, the tail end of the spiral needle rod outer tube is provided with a spiral needle rod fixture for fixing the spiral needle rod outer tube to the fixed groove.

As a preferred embodiment of the spiral soft tissue biopsy needle according to the present invention, the cutting needle rod comprises an cutting needle rod outer tube with a hollow structure which has an outer diameter equal to or smaller than the inner diameter of the sampling outer tube, a cutting edge is arranged on the front end of the cutting needle rod outer tube, and a cutting needle rod fixture for fixing the cutting needle rod outer tube to the fixed groove is provided at the tail end of the cutting needle rod outer tube.

As a preferred embodiment of the spiral soft tissue biopsy needle according to the present invention, the cutting edge has at least two teeth in a triangular or undulating shape in close contact with the outer surface of the spring spiral tube. The multi-group cutting edge teeth can improve the cutting efficiency and shorten the cutting time. The triangular or undulating cutting edge teeth help to cut the sample effectively, and the teeth in close contact with the outer surface of the spring spiral tube enable the formation of shear force between the teeth and the spiral tube thread and thus improve the cutting efficiency.

As a preferred embodiment of the spiral soft tissue biopsy needle according to the present invention, the other end of the spiral needle rod is provided with a rotary rod for rotating the spiral needle rod or cutting needle rod, and the rotary rod and the spiral needle rod fixture are connected through a thread. The rotary rod can rotate the spiral needle rod to the sampling site, and can also drive the cutting needle rod to cut the sample.

As a preferred embodiment of the spiral soft tissue biopsy needle according to the present invention, the fixed groove is provided with a fixed module for positioning the spiral needle rod and the cutting needle rod, the fixed module has a U-shaped cross section and is provided in the middle with a first through hole for the thread to go through, the spiral needle rod fixture and the cutting needle rod fixture are arranged in the cavity composed of the fixed groove and the fixed module, the outer side of the thread on the front end of the rotary rod is provided with a second positioning block for positioning the spiral needle rod and the cutting needle rod. The fixed module is able to position the spring spiral tube, and achieve a quantitative positioning sampling, while can achieve a multi-point one-time sampling in the same line at the same time.

As a preferred embodiment of the spiral soft tissue biopsy needle according to the present invention, the spiral soft tissue biopsy needle further comprises a push rod for pushing the absorbent gelatin into the sampling site, the push rod comprises a round rod, the tail of the round rod is provided with a push rod fixture for positioning the push rod. The push rod is able to push the absorbent gelatin for healing the patient's wound into the sampling site and helps the patient's wound heal.

As a preferred embodiment of the spiral soft tissue biopsy needle according to the present invention, it further comprises a vacuum device, a second through hole connecting with the hollow part of the sampling outer tube is arranged at the upper end of the handle, a first joint is arranged on the outer side of the handle at the upper end of the second through hole, a third through hole connecting with the rear end of the sampling outer tube is arranged at the middle part of the rotary rod, and a second joint is provided at the outer end of the rotary rod at the outer end of the third through hole, and the vacuum device is connected with the first joint or the second joint. In the process of puncture, the vacuum device connected with the first joint can discharge the blood generated in the process of puncture in time, and eliminate the liquid that interferes with the sampling site (such as suppuration after festering) in time, and in the case of good fluidity of the sample of the sampling site, the sampling can be achieved by directly sucking the samples out of the second joint; in the process of positioning and cutting, the vacuum device is connected with the second joint to form negative pressure at the site of the spiral needle rod outer tube or the cutting needle rod outer tube, which is conducive to the cutting of the sample and the separation of the samples from other tissues of the sampling site and thus can improve the accuracy of sampling.

As a preferred embodiment of the spiral soft tissue biopsy needle according to the present invention, the spiral soft tissue biopsy needle further includes a sampling device comprising an upper sampling shell and a lower sampling shell, the upper sampling shell is provided with an upper sampling groove inside, the lower sampling shell is provided with a lower sampling groove inside, the upper sampling groove corresponds to the lower sampling groove in shape and the shape after their closure coincides with the thread shape of the spring spiral tube. After the sampling is finished, the spring spiral tube containing the sample is put into the sampling device, the sampling device is closed, the spring spiral tube is taken out in reverse rotation, the samples will be left in the sampling device, and then the sampling device is opened to give the final samples.

As a preferred embodiment of the spiral soft tissue biopsy needle according to the present invention, the end cutter is made of a memory alloy and the end cutter comprises at least three arc-shaped end cutter blades. The memory alloy allows the end cutter to realize the closing of the blades while the sample needle rod is taken out, thus enabling the cutting of the inner surface of the samples or the excision of the entire small tumor as a whole.

A method of using the spiral soft tissue biopsy needle according to the invention comprises the following steps in the process of sampling large samples or resecting small tumor as a whole:

S01, adjusting the length of the spring spiral rod extending according to the sampling site;

S02, fixing the puncture needle rod on the hand shank and putting the hand shank to puncture to the sampling site;

S03, removing the puncture needle rod from the hand shank and fixing the sampling needle rod on the hand shank;

S04, rotating the sampling needle rod to the sampling site and fixing it, and cutting the sample through the spiral needle rod and cutting needle rod;

S05, taking out both the samples and the sampling needle rod from the hand shank at the same time, and allowing the end cutter to cut the end face of the sample inner side during the taking out process;

S06, separating the samples from the sampling needle rod;

S07, pushing an absorbent gelatin into the sampling site through a push rod.

In the process of sampling large samples or resecting small tumor as a whole performed by the spiral soft tissue biopsy needle according to the invention, as a preferred embodiment, the step S4 further comprises the following steps:

S041, rotating the spiral needle rod through the rotary rod into the sampling site and fixing it;

S042, connecting the vacuum device with the second joint and performing vacuuming;

S043, rotating the cutting needle rod through the rotary rod to cut the side of the sample;

S044, rotating the spiral needle rod through the rotary rod to cut the bottom of the sample;

S045, completing the sampling after taking out the spiral needle rod and cutting needle rod.

In the process of sampling large sample or resecting small tumor as a whole performed by the spiral soft tissue biopsy needle according to the invention, as a preferred embodiment, the step S6 further comprises the following steps:

S061, opening the sampling device and placing the spring spiral tube on the lower sampling groove;

S062, closing the sampling device;

S063, rotating the spring spiral tube in a reverse direction to separate it from the sampling device;

S064, opening the sampling device and taking out the samples.

Since the sampling needle rod of the present invention includes a spiral needle rod for fixing the sampling site and a cutting needle rod for cutting the sample, it can fix the samples of the sampling site first and then take samples by cutting. The sampling can be performed in a quantitative manner based on the length of the spring spiral tube extending at the front end of the spiral needle rod Increasing the length of the spring spiral tube can achieve multi-point sampling in different positions on the same straight line at once.

The present invention further includes a vacuum device, which allows timely discharge of the blood and other interfering liquids (such as suppuration after festering) and improves the accuracy of sampling. It can also form a negative pressure in the spiral needle rod outer tube or the cutting needle rod outer tube, thus increases the efficiency of sampling.

The present invention further includes an end cutter on the outer side of the cutting edge, which can cut the end face of the inner side of a sample, if the sample size is large, to separate the sample from other tissues of the sampling site. It can also cut off a small tumor as a whole.

REFERENCE NUMERALS

1. puncture needle rod; 11. puncture needle; 12. puncture needle rod fixture; 21. spiral needle rod; 211. spring spiral tube; 212. spiral cutting edge; 213. spiral needle rod outer tube; 214. spiral needle rod fixture; 22. cutting needle rod; 221. cutting edge; 222. cutting needle rod outer tube; 223. cutting needle rod fixture; 3. hand shank; 31. handle; 32. sampling outer tube; 33: first positioning block; 34: fixed groove; 4: rotary rod; 41. thread; 5. fixed module; 51: first through hole; 52: second positioning block; 6. push rod; 61: round rod; 62. push rod fixture; 7. vacuum device; 71: second through hole; 72: first joint; 73: third through hole; 74: second joint; 8: sampling device; 81: upper sampling shell; 82. upper sampling groove; 83. lower sampling shell; 84. lower sampling groove; 9. end cutter.

SPECIFIC MODES FOR CARRYING OUT THE EMBODIMENTS

Figure 1:
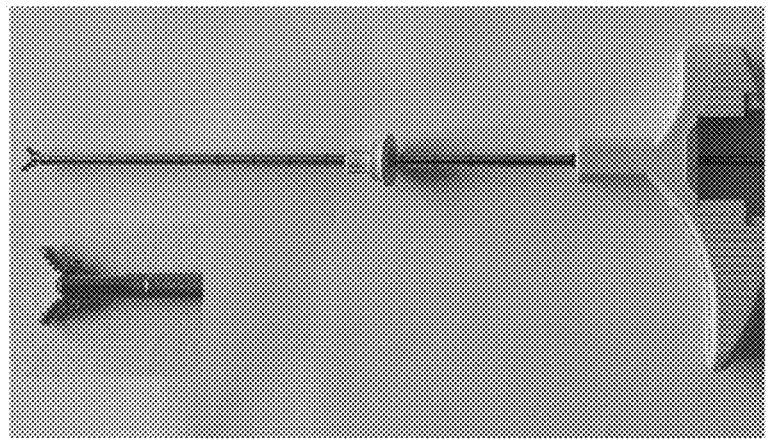
FIG. 1 is a pictorial view of a gripping type biopsy needle in the prior art.
Figure 2:
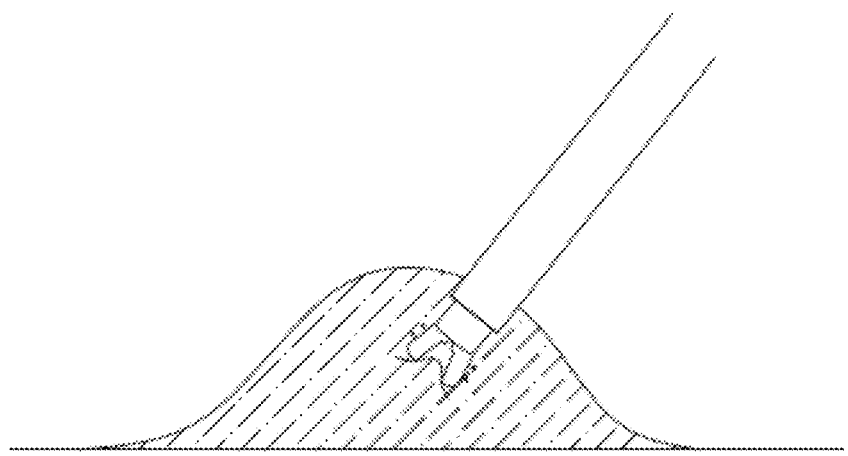
FIG. 2 is a schematic view of a gripping type biopsy needle taking samples.
Figure 2:
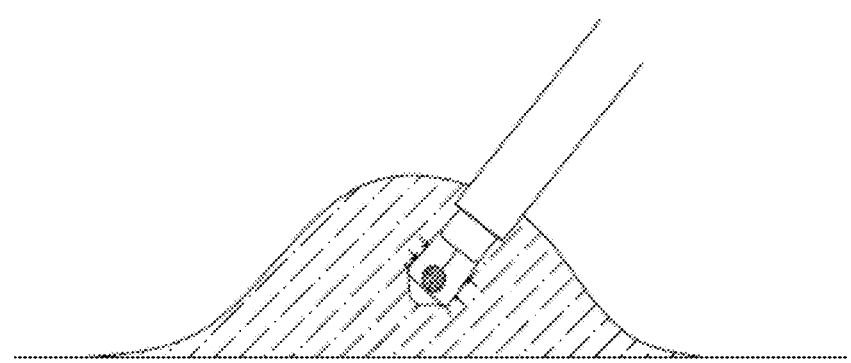
Figure 3:
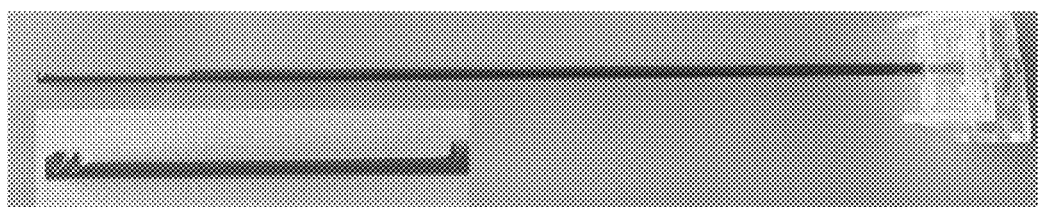
FIG. 3 is a pictorial view of a rotary cutting type biopsy needle in the prior art.
Figure 4:
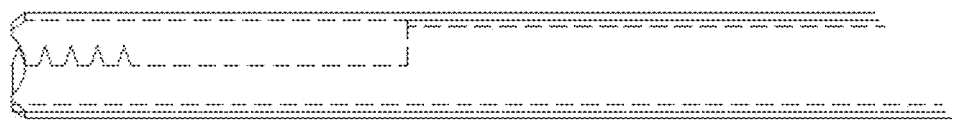
FIG. 4 is the front view of the rotary cutter of a rotary cutting type biopsy needle in the prior art.
Figure 5:
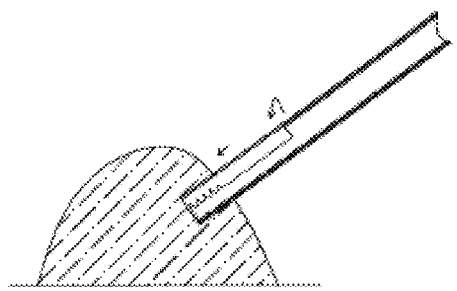
FIG. 5 is a schematic view of a rotary cutting type biopsy needle taking samples.
Figure 5:
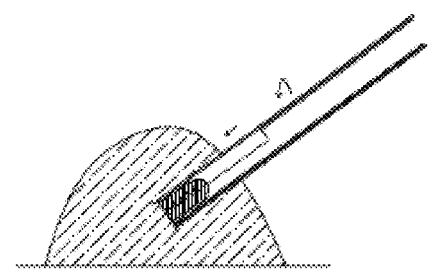
Figure 5:
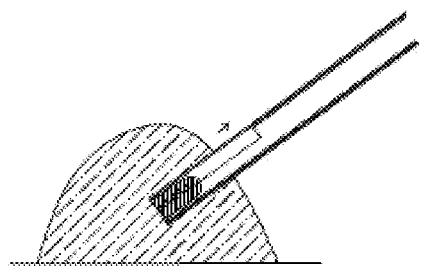
Figure 6:
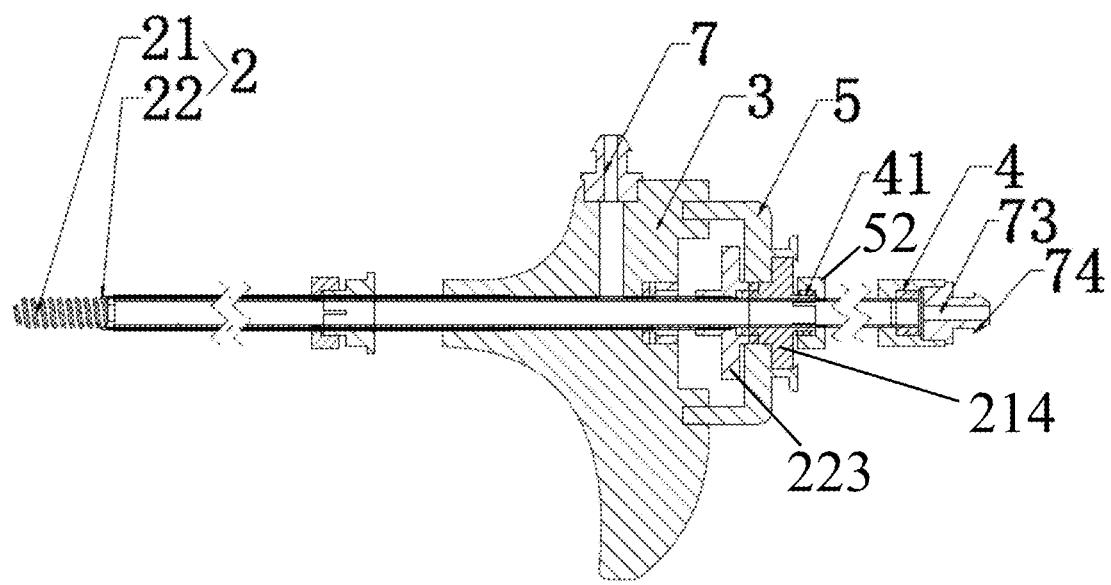
FIG. 6 is the front view of a spiral soft tissue biopsy needle.
Figure 7:
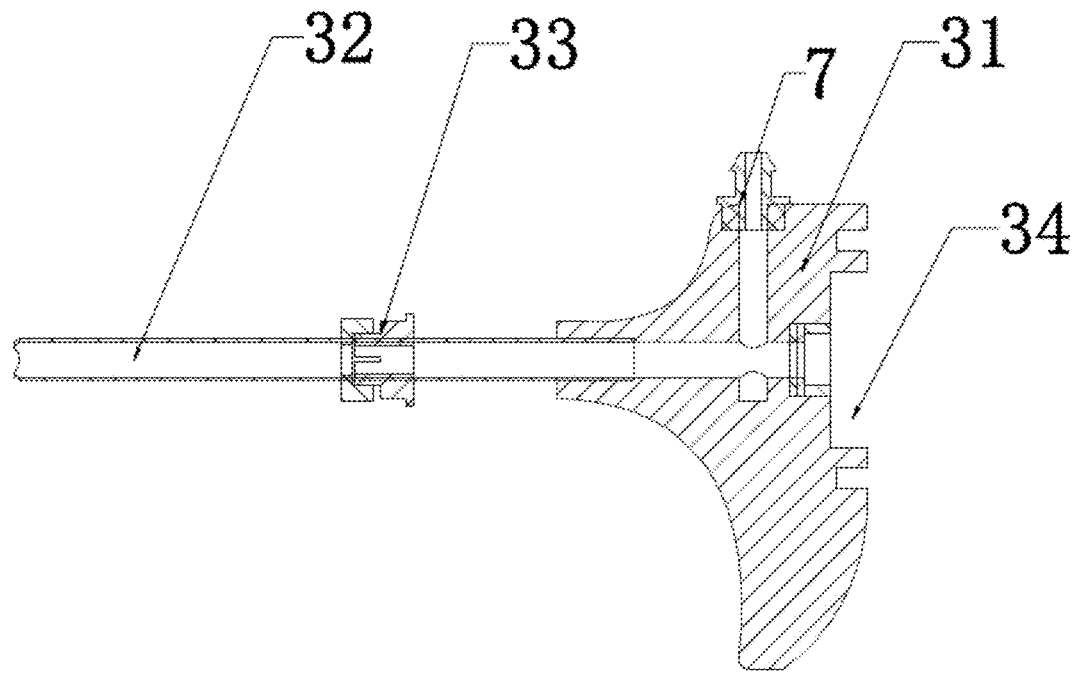
FIG. 7 is the front view of the hand shank of a spiral soft tissue biopsy needle.
Figure 8:
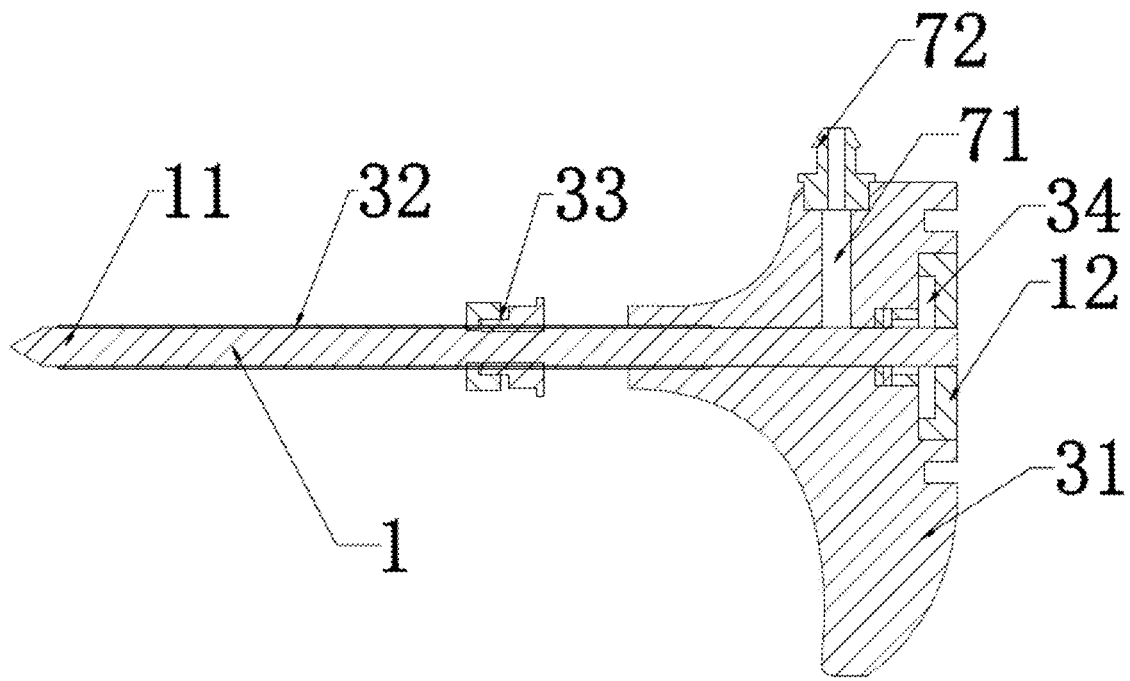
FIG. 8 is an assembly diagram of a puncture needle rod and a hand shank of a spiral soft tissue biopsy needle.
Figure 9:
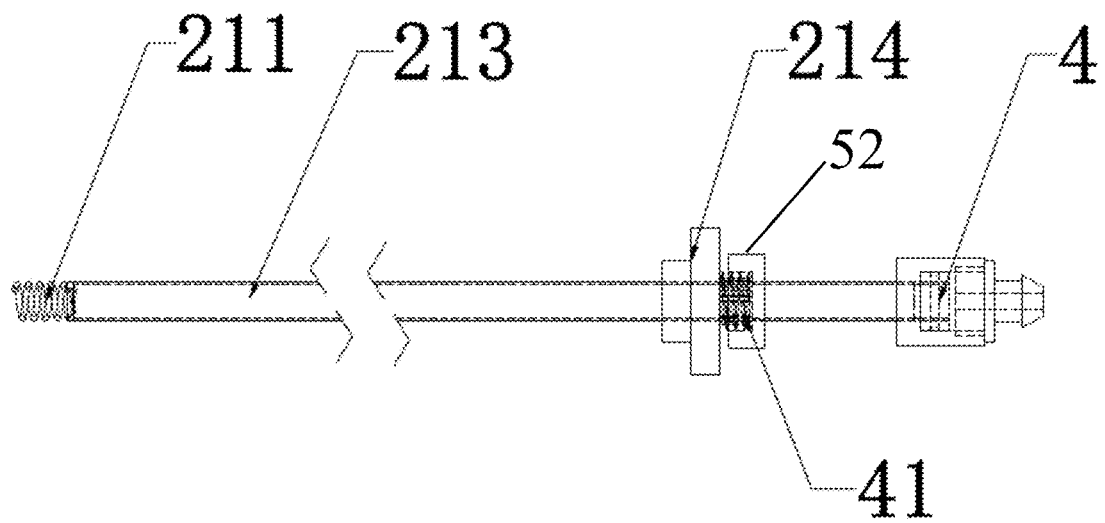
FIG. 9 is an assembly diagram of a puncture needle rod and a rotary rod of a spiral soft tissue biopsy needle.
Figure 10:
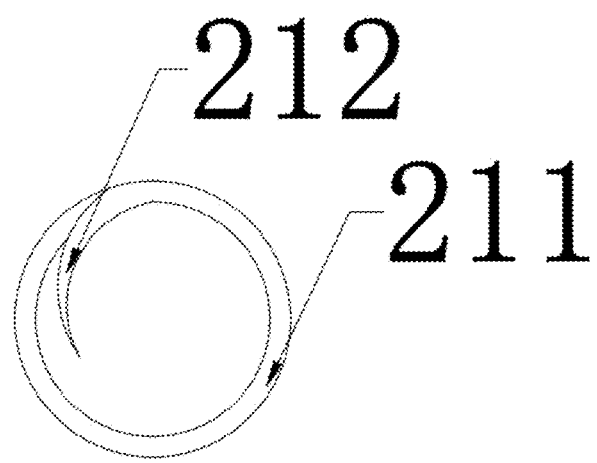
FIG. 10 is the left side view of the spring spiral tube of a spiral soft tissue biopsy needle.
Figure 11:
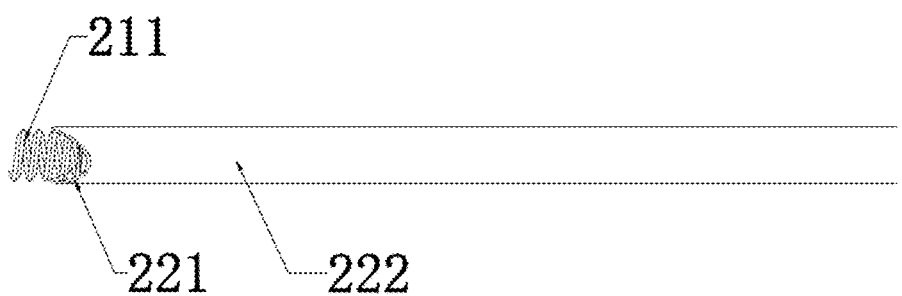
FIG. 11 is an assembly diagram of the spring spiral tube and the cutting edge of example 1 and example 3 of a spiral soft tissue biopsy needle.
Figure 12:
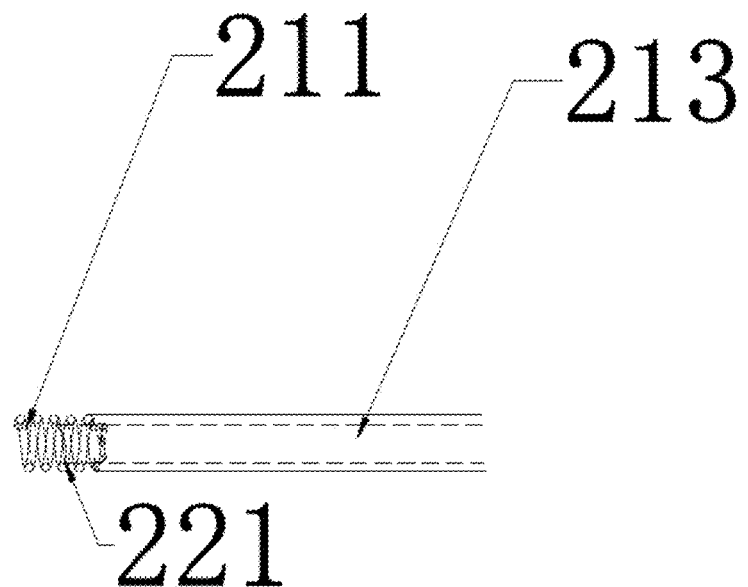
FIG. 12 is an assembly diagram of the spring spiral tube and the cutting edge of example 2 of a spiral soft tissue biopsy needle.
Figure 13:
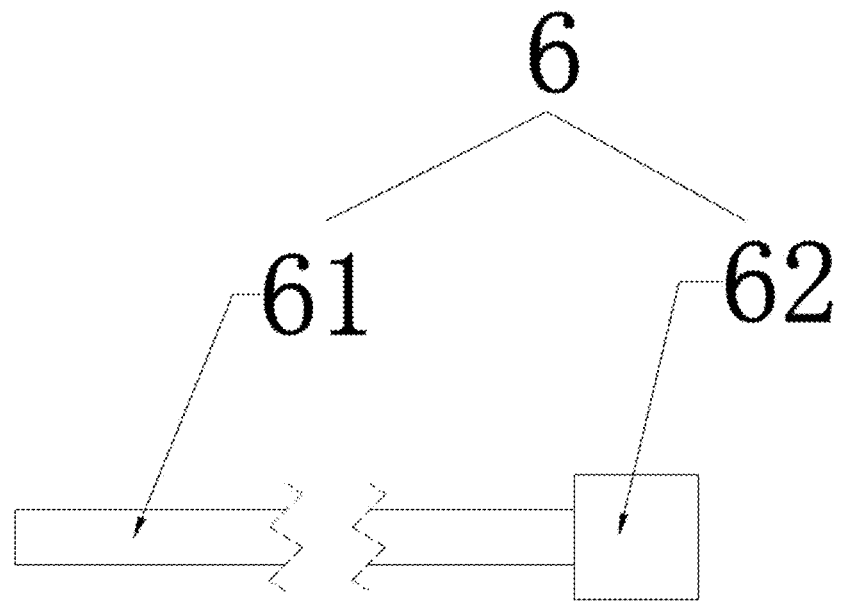
FIG. 13 is the front view of the push rod of a spiral soft tissue biopsy needle.
Figure 14:
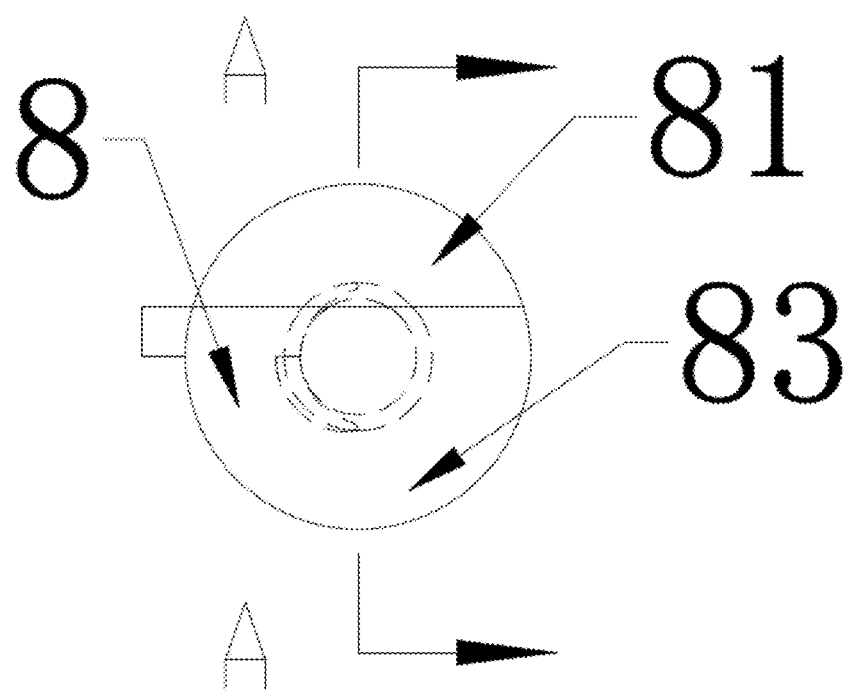
FIG. 14 is the left side view of the sampling device of a spiral soft tissue biopsy needle.
Figure 15:
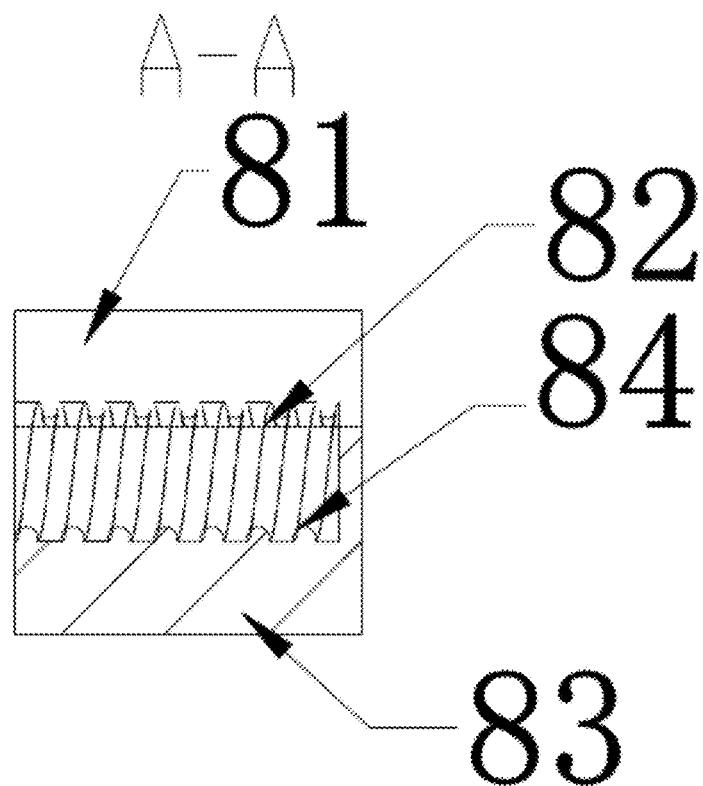
FIG. 15 is the cross-sectional view of the sampling device of a spiral soft tissue biopsy needle.

To achieve sampling of the soft tissue, the present invention provides a spiral soft tissue biopsy needle, as shown in FIG. 6, comprising:

a hand shank 3, as shown in FIG. 7, which comprises a handle 31 which is provided in the middle with a through hole for the puncture needle rod 1 or sampling needle rod 2 to go through, the front end of the handle 31 is provided with a hollow sampling outer tube 32 for directional movement of the puncture needle rod 1 or the sampling needle rod 2, the outer side of the sampling outer tube 33 is provided with a first positioning block 33, the rear end of the handle 31 is provided with a fixed groove 34 for fixing the puncture needle rod 1 or the sampling needle rod 2, and the fixed groove 34 is provided with two steps for fixing the spiral needle rod 21 and the cutting needle rod 22, respectively.

a puncture needle rod 1, which further comprises a puncture needle 11 and a puncture needle rod fixture 12 attached to the tail of the puncture needle 11, the puncture needle 11 has an outer diameter equal to the inner diameter of the sampling outer tube 32. The assembly of the puncture needle 11 and the hand shank 3 is shown in FIG. 8.

a sampling needle rod 2, which comprises a spiral needle rod 21 for fixing the sampling site and a cutting needle rod 22 for separating the samples from the sampling site, the spiral needle rod 21 has a hollow structure, the outer diameter of the spiral needle rod 21 is equal to the inner diameter of the sampling outer tube 32, the front end of the spiral needle rod 21 is provided with a spring spiral tube 211, in order to cut the front end surface of the samples to be sampled, the front end of the spring spiral tube is provided with a spiral cutting edge 212, as shown in FIG. 10, the last thread or the last two threads on the front end of the spring spiral tube 211 has a diameter less than the diameter of the other threads of the spring spiral tube 211. The tail of the spring spiral tube 211 is fixedly connected with a spiral needle rod outer tube 213 with a hollow structure, the spiral needle rod outer tube 213 has an outer diameter equal to the inner diameter of the cutting needle rod outer tube 222 and equal to the outer diameter of the spring spiral tube 211 tail, the tail of the spiral needle rod outer tube 213 is provided with a spiral needle rod fixture 214 for fixing the spiral needle rod outer tube 213 to the fixed groove 34; a cutting needle rod 22 is arranged on the outer side of the spiral needle rod 21 and the inner surface of the cutting needle rod 22 is in close contact with the outer surface of the spiral needle rod 21, the front end of the cutting needle rod 22 is provided with a cutting edge 221, an assembly of the spring spiral tube 211 and the cutting edge 221 is shown in FIG. 11, the cutting needle rod 22 also comprises a cutting needle rod outer tube 222 with a hollow structure which has an outer diameter equal to the inner diameter of the sampling outer tube 32, the cutting edge 221 is arranged on the front end of the cutting needle rod outer tube 222 and has two wavy teeth that are in close contact with the outer surface of the spring spiral tube 211, the tail of the cutting needle rod outer tube 222 is provided with a cutting needle rod fixture 223 for fixing the cutting needle rod outer tube 222 to the fixed groove 34.

a rotary rod 4, which is arranged on the other end of the spiral needle rod fixture 214 and connected with the spiral needle rod fixture 214 through a thread 41, as shown in FIG. 9.

a fixed module 5, which is connected with the fixed groove 34 for positioning the spiral needle rod 21 and the cutting needle rod 22, the fixed module has a U-shaped cross section and is provided in the middle with a first through hole 51 for the thread 41 to go through, the spiral needle rod fixture 214 and the cutting needle rod fixture 223 are arranged in the cavity composed of the fixed groove 34 and the fixed module 5, the outer side of the thread 41 on the front end of the rotary rod 4 is provided with a second positioning block 52 for positioning the spiral needle rod 21 and the cutting needle rod 22.

a push rod 6, which comprises a round rod 61, the tail of the round rod 61 is provided with a push rod fixture 62 for positioning the push rod 6, as shown in FIG. 13.

a vacuum device 7, as shown in FIG. 6, where the upper end of the handle 31 is provided with a second through hole 71 connecting with the hollow part of the sampling outer tube 32, the outer side of the handle 32 at the upper end of the second through hole 71 is provided with a first joint 72, the rotary rod 4 is provided in the middle with a third through hole 73 connecting with the rear end of the sampling outer tube 32, and the outer end of the rotary rod 4 at the outer end of the third through hole 73 is provided with a second joint 74, and the vacuum device 7 is connected with the first joint 72 or the second joint 74.

a sampling device 8, as shown in FIGS. 14-15, which comprises an upper sampling shell 81 and a lower sampling shell 83, the upper sampling shell 81 is provided with an upper sampling groove 82 inside, the lower sampling shell 83 is provided with a lower sampling groove 84 inside, the upper sampling groove 82 corresponds to the lower sampling groove 84 in shape and the shape after their closure coincides with the thread shape of the spring spiral tube 211.

Figure 21:
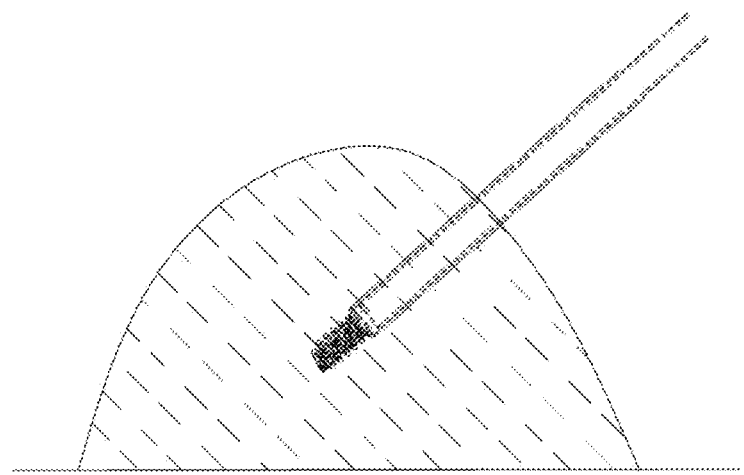
FIG. 21 is a schematic diagram of using the spiral needle rod of a spiral soft tissue biopsy needle.
Figure 22:
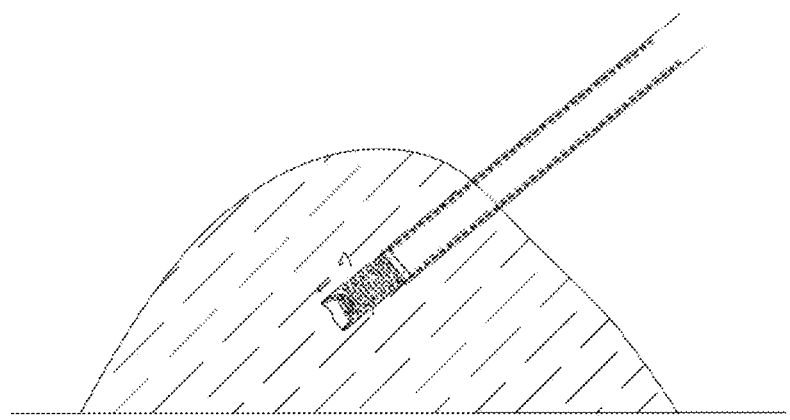
FIG. 22 is a schematic diagram of using the cutting needle rod of a spiral soft tissue biopsy needle.
Figure 23:
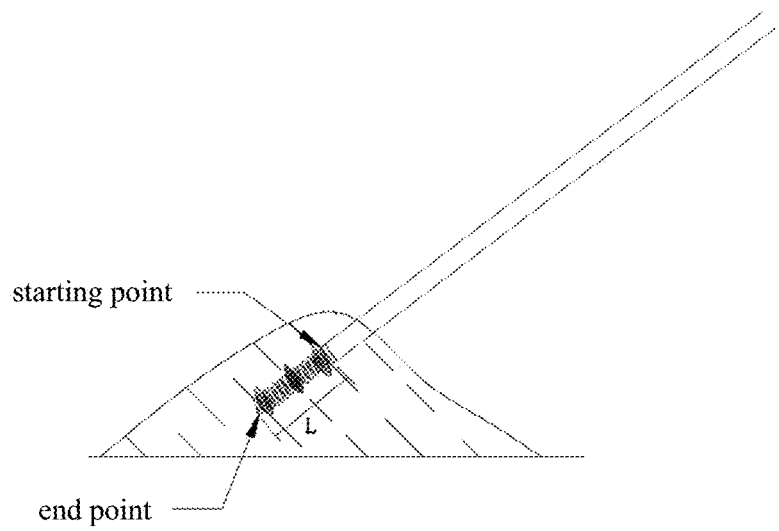
FIG. 23 is a schematic diagram of a spiral soft tissue biopsy needle multi-point continuous sampling.
Figure 24:
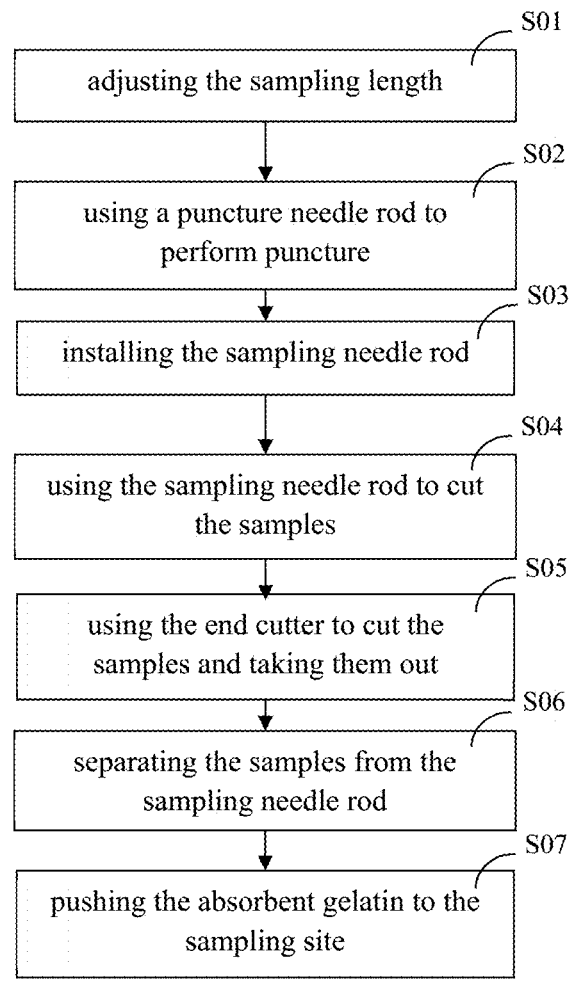
FIG. 24 is a flow chart of a method of using a spiral soft tissue biopsy needle with an end cutter.
Figure 25:
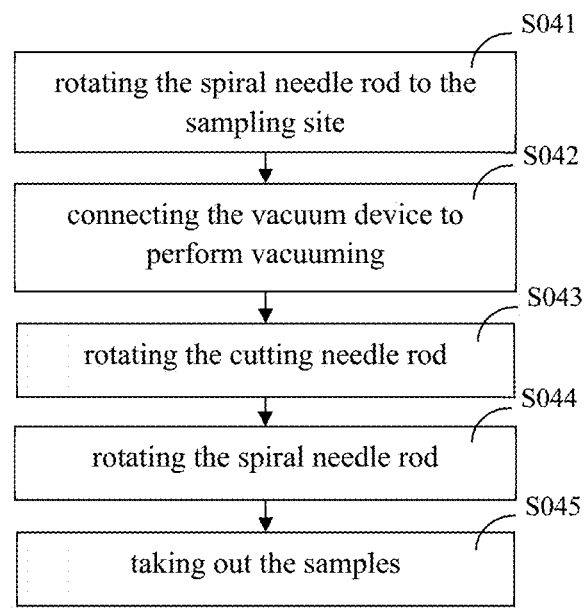
FIG. 25 is a flow chart of step S04 of a method of using a spiral soft tissue biopsy needle with an end cutter.
Figure 26:
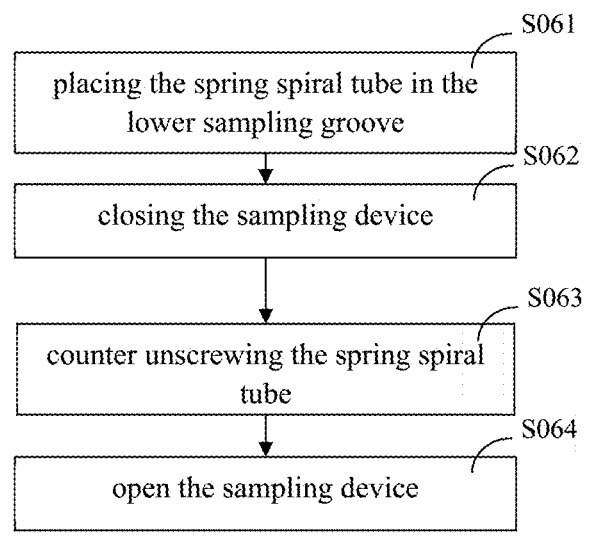
FIG. 26 is a flow chart of step S06 of a method of using a spiral soft tissue biopsy needle with an end cutter.

As shown in FIGS. 17 to 20, a process of using the spiral soft tissue biopsy needle according to the present invention comprises the following steps:

S1, adjusting the sampling length of the sampling needle rod 2 according to the sampling requirements; comprising S11, connecting the spiral needle rod 21 with the cutting needle rod 22 and fixedly connecting the spiral needle rod fixture 214 with the fixed module 5;

S12, connecting the fixed module 5 with the hand shank 3 fixedly;

S13, adjusting the sampling length by adjusting the length of the spring spiral rod extending out of the cutting needle rod 22;

S2, fixing the puncture needle rod 1 on the hand shank 3 and putting the hand shank 3 to puncture to the sampling site;

S3, removing the puncture needle rod 1 from the hand shank 3 and fixing the sampling needle rod 2 on the hand shank 3;

S4, taking samples according to the sampling length adjusted in S1, as shown in FIGS. 21 to 23, comprising S41, rotating the spiral needle rod 21 through the rotary rod 4 into the sampling site and fixing it;

S42, connecting the vacuum device 7 with the second joint 74 and performing vacuuming;

S43, rotating the cutting needle rod 22 through the rotary rod 4 to cut the side of the sample;

S44, rotating the spiral needle rod 21 through the rotary rod 4 to cut the bottom of the sample;

S45, completing the sampling after taking out the spiral needle rod 21 and cutting needle rod 22;

S5, taking out both the samples and the sampling needle rod 2 from the hand shank 3 at the same time;

S6, separating the samples from the sampling needle rod 2; comprising

S61, opening the sampling device 8 and placing the spring spiral tube 211 on the lower sampling groove 84;

S62, closing the sampling device 8;

S63, rotating the spring spiral tube 211 in a reverse direction to separate it from the sampling device 8;

S64, opening the sampling device 8 and taking out the samples;

S7, pushing an absorbent gelatin into the sampling site through the push rod 6.

Example 1

The sampling of a muscle tissue comprises the following steps:

S11, connecting the spiral needle rod 21 with the cutting needle rod 22 and fixedly connecting the spiral needle rod fixture 214 with the fixed module 5;

S12, connecting the fixed module 5 with the hand shank 3 fixedly;

S13, adjusting the sampling length by adjusting the length of the spring spiral rod 211 extending out of the cutting needle rod 22, wherein the diameter of the spring spiral tube 211 is selected to be 1 mm, quantitative sampling can be achieved based on the diameter of the spring spiral tube 211 and its length of extending;

S14, fixing the puncture needle rod 1 on the hand shank 3 and putting the hand shank 3 to puncture to the sampling site;

S15, removing the puncture needle rod 1 from the hand shank 3 and fixing the sampling needle rod 2 on the hand shank 3;

S16, rotating the spiral needle rod 21 through the rotary rod 4 into the sampling site and fixing it;

S17, rotating the cutting needle rod 22 through the rotary rod 4 to cut the side of the sample, where in the process of cutting, the cutting edge 221 is in close contact with the thread of the spring spiral tube 211, thus generating a shear force to cut the samples smoothly;

S18, rotating the spiral needle rod 21 through the rotary rod 4 to cut the bottom of the samples;

S19, taking out the spiral needle rod 21 and cutting needle rod 22, thereby completing the sampling;

S110, pushing an absorbent gelatin into the sampling site through the push rod 6, where after taking out the push rod 6 and the sampling outer tube 32, the tissue of the sampling site can automatically close the absorbent gelatin inside the wound caused by the sampling, which helps the recovery of wound caused by the sampling.

Figure 28:
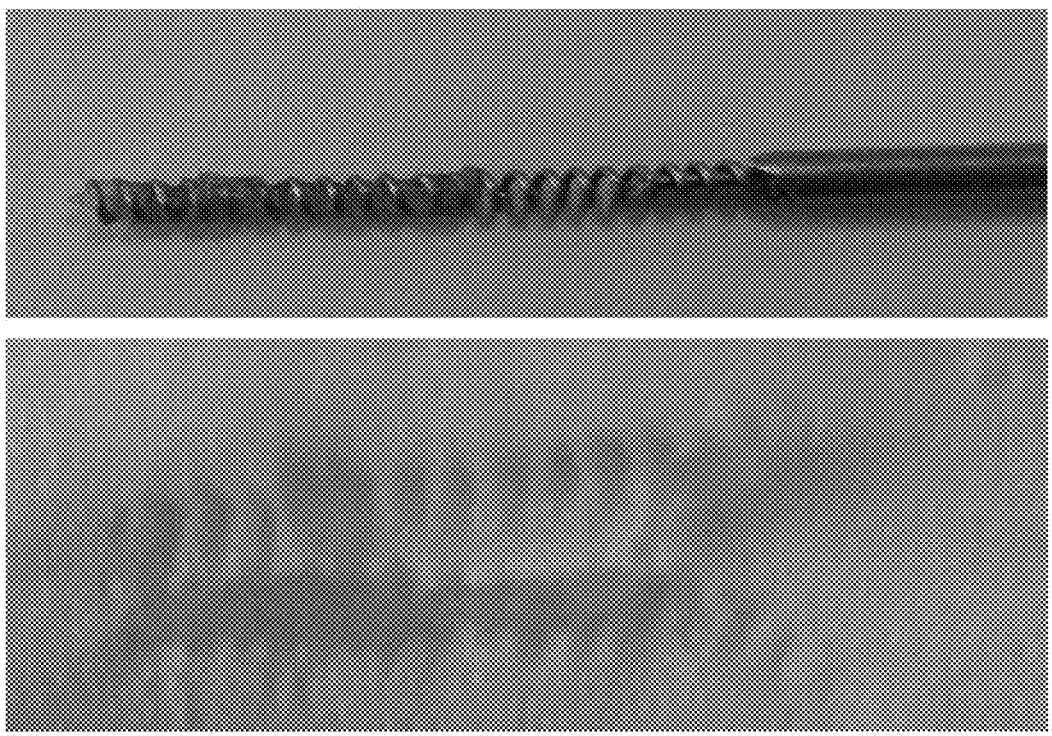
FIG. 28 is a diagram showing the effect of sampling of the spiral soft tissue biopsy needle of examples 1 to 3.

The sampling effect of the present example is shown in FIG. 28. It can be seen that the samples have good integrity and continuity, and provides a good stock sample for further analysis of the sample such as sample slicing, and positioning analysis, etc.

Example 2

In order to reduce the bleeding of the tissue during the puncture, the present example adds a vacuum device for the sampling of the muscle tissue, comprising the steps of:

S21, connecting the spiral needle rod 21 with the cutting needle rod 22 and fixedly connecting the spiral needle rod fixture 214 with the fixed module 5;

S22, connecting the fixed module 5 with the hand shank 3 fixedly;

S23, adjusting the sampling length by adjusting the length of the spring spiral rod 211 extending out of the cutting needle rod 22, wherein the diameter of the spring spiral tube 211 is selected to be 1 mm, quantitative sampling can be achieved by the diameter of the spring spiral tube 211 and its length of extending;

S24, connecting the vacuum device 7 with the first joint 72 and performing vacuuming;

S25, under vacuuming, fixing the puncture needle rod 1 on the hand shank 3 and fixing the puncture needle rod 1 on the hand shank 3 and putting the hand shank 3 to puncture to the sampling site, the blood generated during puncture is drawn from the first joint 72;

S26, removing the puncture needle rod 1 from the hand shank 3 and fixing the sampling needle rod 2 on the hand shank 3;

S27, connecting the vacuum device 7 with the second joint 74 and performing vacuuming;

S28, under vacuuming, rotating the spiral needle rod 21 through the rotary rod 4 into the sampling site and fixing it;

S29, under vacuuming, rotating the cutting needle rod 22 through the rotary rod 4 to cut the side of the samples, where in the process of cutting, the cutting edge 221 is in close contact with the thread of the spring spiral tube 211, thus generating a shear force to cut the samples regularly;

S210, under vacuuming, rotating the spiral needle rod 21 through the rotary rod 4 to cut the bottom of the samples;

S211, completing the sampling after taking out the spiral needle rod 21 and cutting needle rod 22;

S212, pushing an absorbent gelatin into the sampling site through the push rod 6, where after taking out the push rod 6 and the sampling outer tube 32, the tissue of the sampling site can automatically close the absorbent gelatin inside the sampling wounds, which is conducive to the recovery of sampling wounds.

The sampling effect of the present example is shown in FIG. 28, and it can be seen that the sample obtained has good integrity and continuity, which provides a good stock sample for further analysis, such as sample slicing, and localization analysis, etc.

Example 3

In order to facilitate the sampling, the present example adds a sampling device for sampling of the muscle tissue, comprising the steps of:

S31, connecting the spiral needle rod 21 with the cutting needle rod 22 and fixedly connecting the spiral needle rod fixture 214 with the fixed module 5;

S32, connecting the fixed module 5 with the hand shank 3 fixedly;

S33, adjusting the sampling length by adjusting the length of the spring spiral rod 211 extending out of the cutting needle rod 22, where the diameter of the spring spiral tube 211 is selected to be 1 mm, a quantitative sampling can be achieved by the diameter of the spring spiral tube 211 and its length of extending;

S34, connecting the vacuum device 7 with the first joint 72 and performing vacuuming;

S35, under vacuuming, fixing the puncture needle rod 1 on the hand shank 3 and fixing the puncture needle rod 1 on the hand shank 3 and putting the hand shank 3 to puncture to the sampling site, where the blood generated in the process of puncture is drawn from the first joint 72;

S36, removing the puncture needle rod 1 from the hand shank 3 and fixing the sampling needle rod 2 on the hand shank 3;

S37, connecting the vacuum device 7 with the second joint 74 and performing vacuuming;

S38, under vacuuming, rotating the spiral needle rod 21 through the rotary rod 4 into the sampling site and fixing it;

S39, under vacuuming, rotating the cutting needle rod 22 through the rotary rod 4 to cut the side of the samples, where in the process of cutting, the cutting edge 221 is in close contact with the thread of the spring spiral tube 211, thus forming a shear force to cut the samples regularly;

S310, under vacuuming, rotating the spiral needle rod 21 through the rotary rod 4 to cut the bottom of the samples;

S311, completing the sampling after taking out the spiral needle rod 21 and cutting needle rod 22;

S312, taking out the samples and the sampling needle rod 2 from the hand shank 3 at the same time;

S313, opening the sampling device 8, placing the spring spiral tube 211 on the lower sampling groove 84 and closing the sampling device 8;

S314, rotating the spring spiral tube 211 in a reverse direction to separate it from the sampling device 8;

S315, opening the sampling device 8 and taking out the samples.

S316, pushing an absorbent gelatin into the sampling site through the push rod 6, where after taking out the push rod 6 and the sampling outer tube 32, the tissue of the sampling site can automatically close the absorbent gelatin inside the sampling wounds, which is conducive to the recovery of sampling wounds.

The sampling effect of the present example is shown in FIG. 28, and it can be seen that the sample obtained has good integrity and continuity, which provides a good stock sample for the further detection of samples such as sample slicing, and localization analysis, etc.

Example 4

In order to achieve multiple-point continuous sampling, the length of the spring spiral rod 211 extending out of the cutting needle rod 22 can be increased for sampling the muscle tissue. The process comprises the steps of:

S41, connecting the spiral needle rod 21 with the cutting needle rod 22 and fixedly connecting the spiral needle rod fixture 214 with the fixed module 5;

S42, connecting the fixed module 5 with the hand shank 3 fixedly;

S43, adjusting the sampling length by adjusting the length of the spring spiral rod 211 extending out of the cutting needle rod 22, wherein the diameter of the spring spiral tube 211 is selected to be 1 mm, quantitative sampling can be achieved by the diameter of the spring spiral tube 211 and its length of extending, multiple-point continuous sampling can be achieved by increasing the length of the spring spiral rod 211 extending out of the cutting needle rod 22;

S44, connecting the vacuum device 7 with the first joint 72 and performing vacuuming;

S45, under vacuuming, fixing the puncture needle rod 1 on the hand shank 3 and fixing the puncture needle rod 1 on the hand shank 3 and putting the hand shank 3 to puncture to the sampling site, the blood generated in the process of puncture is drawn from the first joint 72;

S46, removing the puncture needle rod 1 from the hand shank 3 and fixing the sampling needle rod 2 on the hand shank 3;

S47, connecting the vacuum device 7 with the second joint 74 and performing vacuuming;

S48, under vacuuming, rotating the spiral needle rod 21 through the rotary rod 4 into the sampling site and fixing it;

S49, under vacuuming, rotating the cutting needle rod 22 through the rotary rod 4 to cut the side of the samples, where in the process of cutting, the cutting edge 221 is in close contact with the thread of the spring spiral tube 211, which forms a shear force to cut the samples regularly;

S410, under vacuuming, rotating the spiral needle rod 21 through the rotary rod 4 to cut the bottom of the samples;

S411, completing the sampling after taking out the spiral needle rod 21 and cutting needle rod 22;

S412, taking out the samples and the sampling needle rod 2 from the hand shank 3 at the same time;

S413, opening the sampling device 8, placing the spring spiral tube 211 on the lower sampling groove 84 and closing the sampling device 8;

S414, rotating the spring spiral tube 211 in a reverse direction to separate it from the sampling device 8;

S415, opening the sampling device 8 and taking out the samples.

S416, pushing an absorbent gelatin into the sampling site through the push rod 6, wherein, after taking out the push rod 6 and the sampling outer tube 32, the tissue of the sampling site can automatically close the absorbent gelatin inside the sampling wounds, which is conducive to the recovery of sampling wounds.

Figure 29:
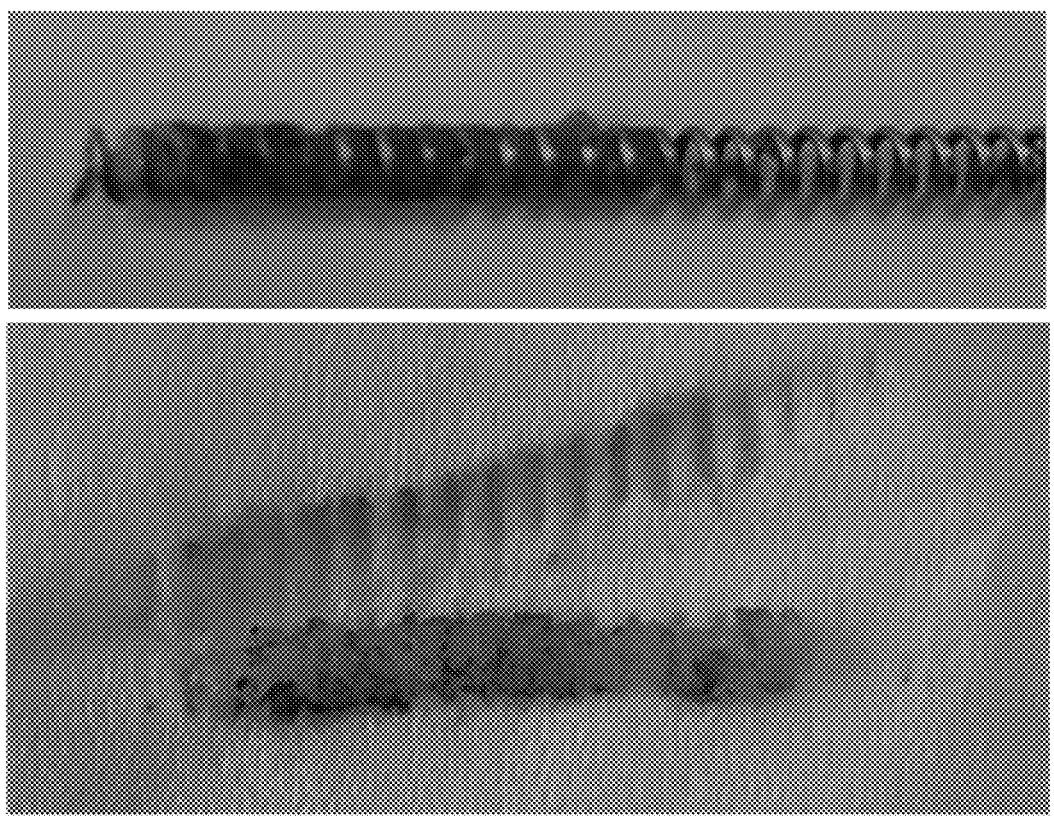
FIG. 29 is a diagram showing the effect of sampling of the spiral soft tissue biopsy needle of example 4.

The sampling effect of the present example is shown in FIG. 29, and it can be seen that the sample obtained has good integrity and continuity, which provides a good stock sample for further analysis such as sample slicing, and localization analysis, etc.

Example 5

The spiral soft tissue biopsy of needle the present example can take samples from different tissues including liver tissue, comprising the steps of:

S51, connecting the spiral needle rod 21 with the cutting needle rod 22 and fixedly connecting the spiral needle rod fixture 214 with the fixed module 5;

S52, connecting the fixed module 5 with the hand shank 3 fixedly;

S53, adjusting the sampling length by adjusting the length of the spring spiral rod 211 extending out of the cutting needle rod 22, wherein the diameter of the spring spiral tube 211 is selected to be 2 mm, quantitative sampling can be achieved by the diameter of the spring spiral tube 211 and its length of extending, multiple-point continuous sampling can be achieved by increasing the length of the spring spiral rod 211 extending out of the cutting needle rod 22;

S54, connecting the vacuum device 7 with the first joint 72 and performing vacuuming;

S55, under vacuuming, fixing the puncture needle rod 1 on the hand shank 3 and fixing the puncture needle rod 1 on the hand shank 3 and putting the hand shank 3 to puncture to the sampling site, where the blood generated in the process of puncture is drawn from the first joint 72;

S56, removing the puncture needle rod 1 from the hand shank 3 and fixing the sampling needle rod 2 on the hand shank 3;

S57, connecting the vacuum device 7 with the second joint 74 and performing vacuuming;

S58, under vacuuming, rotating the spiral needle rod 21 through the rotary rod 4 into the sampling site and fixing it;

S59, under vacuuming, rotating the cutting needle rod 22 through the rotary rod 4 to cut the side of the samples, where in the process of cutting, the cutting edge 221 is in close contact with the thread of the spring spiral tube 211, which forms a shear force to cut the samples regularly;

S510, under vacuuming, rotating the spiral needle rod 21 through the rotary rod 4 to cut the bottom of the samples;

S511, taking out the spiral needle rod 21 and cutting needle rod 22, thereby completing the sampling;

S512, taking out the samples and the sampling needle rod 2 from the hand shank 3 at the same time;

S513, opening the sampling device 8, placing the spring spiral tube 211 on the lower sampling groove 84 and closing the sampling device 8;

S514, rotating the spring spiral tube 211 in a reverse direction to separate it from the sampling device 8;

S515, opening the sampling device 8 and taking out the samples.

S516, pushing an absorbent gelatin into the sampling site through the push rod 6, wherein, after taking out the push rod 6 and the sampling outer tube 32, the tissue of the sampling site can automatically close the absorbent gelatin inside the sampling wounds, which is conducive to the recovery of sampling wounds.

Figure 30:
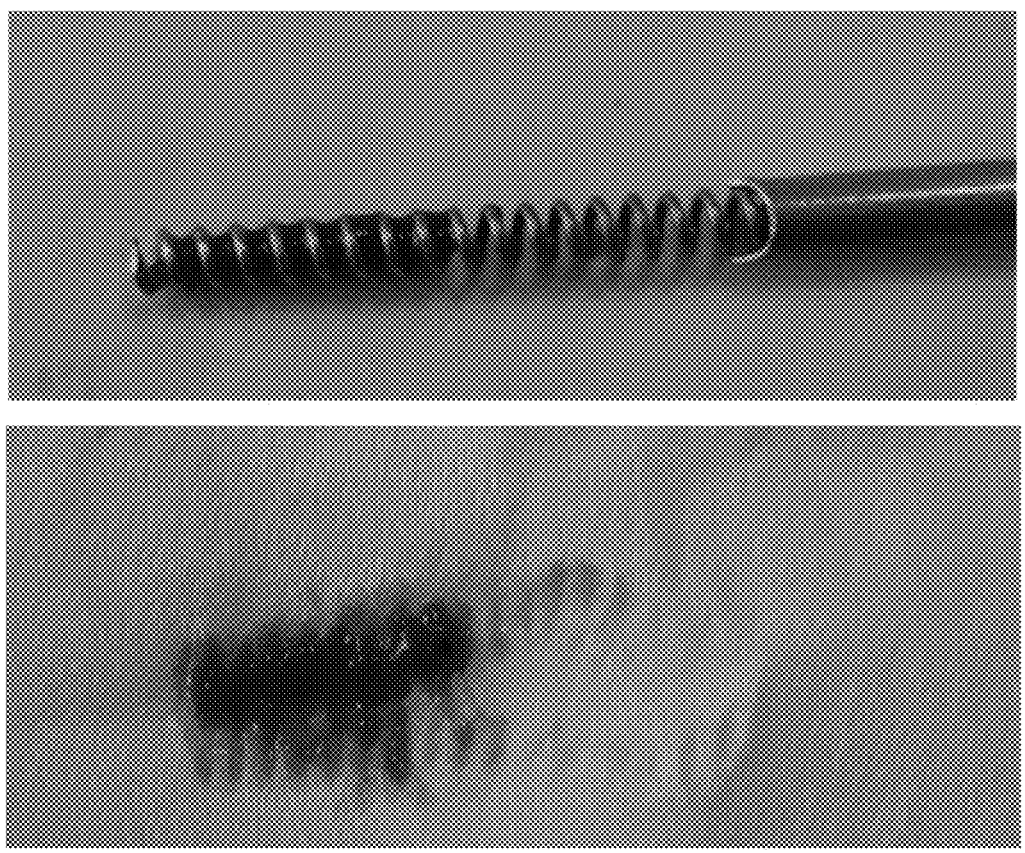
FIG. 30 is a diagram showing the effect of sampling of the spiral soft tissue biopsy needle of example 5.

The sampling effect of the present example is shown in FIG. 30, and it can be seen that the sample obtained has good integrity and continuity, which provides a good stock sample for the further analysis such as sample slicing, and localization analysis, etc.

To achieve sampling of large samples, the present invention provides a spiral soft tissue biopsy needle, as shown in FIG. 6, comprising:

a hand shank 3, as shown in FIG. 7, it comprises a handle 31 which is provided in the middle with a through hole for the puncture needle rod 1 or sampling needle rod 2 to go through, the front end of the handle 31 is provided with a hollow sampling outer tube 32 for directional movement of the puncture needle rod 1 or the sampling needle rod 2, the outer side of the sampling outer tube 33 is provided with a first positioning block 33, the rear end of the handle 31 is provided with a fixed groove 34 for fixing the puncture needle rod 1 or the sampling needle rod 2, and the fixed groove 34 is provided with two steps for fixing the spiral needle rod 21 and the cutting needle rod 22, respectively.

a puncture needle rod 1, which further comprises a puncture needle 11 and a puncture needle rod fixture 12 attached to the tail of the puncture needle 11, the outer diameter of the puncture needle 11 has an outer diameter of equal to the inner diameter of the sampling outer tube 32. The assembly of the puncture needle 11 and the hand shank 3 is shown in FIG. 8.

a sampling needle rod 2, which comprises a spiral needle rod 21 for fixing the sampling site and a cutting needle rod 22 for separating the sample from the sampling site, the spiral needle rod 21 has a hollow structure and has an outer diameter equal to the inner diameter of the sampling outer tube 32, the front end of the spiral needle rod 21 is provided with a spring spiral tube 211, in order to cut the front end surface of the samples to be sampled, the front end of the spring spiral tube is provided with a spiral cutting edge 212, as shown in FIG. 10. The tail of the spring spiral tube 211 is fixedly connected with a spiral needle rod outer tube 213 with a hollow structure, the spiral needle rod outer tube 213 has an inner diameter equal to the outer diameter of the cutting needle rod outer tube 222 and equal to the inner diameter of the spring spiral tube 211 tail, the tail of the spiral needle rod outer tube 213 is provided with a spiral needle rod fixture 214 for fixing the spiral needle rod outer tube 213 to the fixed groove 34; a cutting needle rod 22 is arranged on the inner side of the spiral needle rod 21 and the outer surface of the cutting needle rod 22 is in close contact with the inner surface of the spiral needle rod 21, the front end of the cutting needle rod 22 is provided with a cutting edge 221, an assembly of the spring spiral tube 211 and the cutting edge 221 is shown in FIG. 11, the cutting needle rod 22 also comprises a cutting needle rod outer tube 222 with a hollow structure which has an outer diameter equal to the inner diameter of the spiral needle rod outer tube 213, the cutting edge 221 is arranged on the front end of the cutting needle rod outer tube 222 and has two wavy teeth that are in close contact with the outer surface of the spring spiral tube 211, the tail of the cutting needle rod outer tube 222 is provided with a cutting needle rod fixture 223 for fixing the cutting needle rod outer tube 222 to the fixed groove 34.

a rotary rod 4, which is arranged on the other end of the spiral needle rod fixture 214 and connected with the spiral needle rod fixture 214 through a thread 41, as shown in FIG. 9.

a fixed module 5, which is connected with the fixed groove 34 for positioning the spiral needle rod 21 and the cutting needle rod 22, the fixed module 5 has a U-shaped cross section and is provided in the middle with a first through hole 51 for the thread 41 to go through, the spiral needle rod fixture 214 and the cutting needle rod fixture 223 are arranged in the cavity composed of the fixed groove 34 and the fixed module 5, the outer side of the thread 41 on the front end of the rotary rod 4 is provided with a second positioning block 52 for positioning the spiral needle rod 21 and the cutting needle rod 22.

a push rod 6, which comprises a round rod 61, the tail of the round rod 61 is provided with a push rod fixture 62 for positioning the push rod 6, as shown in FIG. 13.

a vacuum device 7, as shown in FIG. 6, where the upper end of the handle 31 is provided with a second through hole 71 connecting with the hollow part of the sampling outer tube 32, the outer side of the handle 32 at the upper end of the second through hole 71 is provided with a first joint 72, the rotary rod 4 is provided in the middle with a third through hole 73 connecting with the rear end of the sampling outer tube 32, and the outer end of the rotary rod 4 at the outer end of the third through hole 73 is provided with a second joint 74, and the vacuum device 7 is connected with the first joint 72 or the second joint 74.

a sampling device 8, as shown in FIGS. 14-15, which comprises an upper sampling shell 81 and a lower sampling shell 83, the upper sampling shell 81 is provided with an upper sampling groove 82 inside, the lower sampling shell 83 is provided with a lower sampling groove 84 inside, the upper sampling groove 82 corresponds to the lower sampling groove 84 in shape and the shape after their closure coincides with the thread shape of the spring spiral tube 211.

As shown in FIGS. 17 to 20, the spiral soft tissue biopsy needle according to the present invention comprises the following steps in the process of use:

S1, adjusting the sampling length of the sampling needle rod 2 according to the sampling requirements; comprising S11, connecting the spiral needle rod 21 with the cutting needle rod 22 and fixedly connecting the spiral needle rod fixture 214 with the fixed module 5;

S12, connecting the fixed module 5 with the hand shank 3 fixedly;

S13, adjusting the sampling length by adjusting the length of the spring spiral rod extending out of the cutting needle rod 22.

S2, fixing the puncture needle rod 1 on the hand shank 3 and putting the hand shank 3 to puncture to the sampling site;

S3, removing the puncture needle rod 1 from the hand shank 3 and fixing the sampling needle rod 2 on the hand shank 3;

S4, taking samples according to the sampling length adjusted in S1, as shown in FIGS. 21 to 23; comprising S41, rotating the spiral needle rod 21 through the rotary rod 4 into the sampling site and fixing it;

S42, connecting the vacuum device 7 with the second joint 74 and performing vacuuming;

S43, rotating the cutting needle rod 22 through the rotary rod 4 to cut the side of the samples;

S44, rotating the spiral needle rod 21 through the rotary rod 4 to cut the bottom of the samples;

S45, taking out the spiral needle rod 21 and cutting needle rod 22, thereby completing the sampling;

S5, taking out the samples and the sampling needle rod 2 from the hand shank 3 at the same time;

S6, separating the samples from the sampling needle rod 2; comprising

S61, opening the sampling device 8 and placing the spring spiral tube 211 on the lower sampling groove 84;

S62, closing the sampling device 8;

S63, rotating the spring spiral tube 211 in a reverse direction to separate it from the sampling device 8;

S64, opening the sampling device 8 and taking out the samples.

S7, pushing an absorbent gelatin into the sampling site through the push rod 6.

Example 6

To achieve sampling of large samples, muscle tissue, a spring spiral tube 211 with large diameter is selected and the cutting edge 221 is arranged in the spring spiral tube 211, the sampling comprises the steps of:

S61, connecting the spiral needle rod 21 with the cutting needle rod 22 and fixedly connecting the spiral needle rod fixture 214 with the fixed module 5;

S62, connecting the fixed module 5 with the hand shank 3 fixedly;

S63, adjusting the sampling length by adjusting the length of the spring spiral rod 211 extending out of the cutting needle rod 22, wherein the diameter of the spring spiral tube 211 is selected to be 3 mm, a quantitative sampling can be achieved by the diameter of the spring spiral tube 211 and its length of extending, multiple-point continuous sampling can be achieved by increasing the length of the spring spiral rod 211 extending out of the cutting needle rod 22;

S64, connecting the vacuum device 7 with the first joint 72 and performing vacuuming;

S65, under vacuuming, fixing the puncture needle rod 1 on the hand shank 3 and fixing the puncture needle rod 1 on the hand shank 3 and putting the hand shank 3 to puncture to the sampling site, where the blood generated in the process of puncture is drawn from the first joint 72;

S66, removing the puncture needle rod 1 from the hand shank 3 and fixing the sampling needle rod 2 on the hand shank 3;

S67, connecting the vacuum device 7 with the second joint 74 and performing vacuuming;

S68, under vacuuming, rotating the spiral needle rod 21 through the rotary rod 4 into the sampling site and fixing it;

S69, under vacuuming, rotating the cutting needle rod 22 through the rotary rod 4 to cut the side of the samples, where in the process of cutting, the cutting edge 221 is in close contact with the thread of the spring spiral tube 211, which forms a shear force to cut the samples regularly;

S610, under vacuuming, rotating the spiral needle rod 21 through the rotary rod 4 to cut the bottom of the sample;

S611, taking out the spiral needle rod 21 and cutting needle rod 22, thereby completing the sampling;

S612, taking out the samples and the sampling needle rod 2 from the hand shank 3 at the same time;

S613, opening the sampling device 8, placing the spring spiral tube 211 on the lower sampling groove 84 and closing the sampling device 8;

S614, rotating the spring spiral tube 211 in a reverse direction to separate it from the sampling device 8;

S615, opening the sampling device 8 and taking out the samples;

S616, pushing an absorbent gelatin into the sampling site through the push rod 6, wherein, after taking out the push rod 6 and the sampling outer tube 32, the tissue of the sampling site can automatically close the absorbent gelatin inside the sampling wounds, which is conducive to the recovery of sampling wounds.

Figure 31:
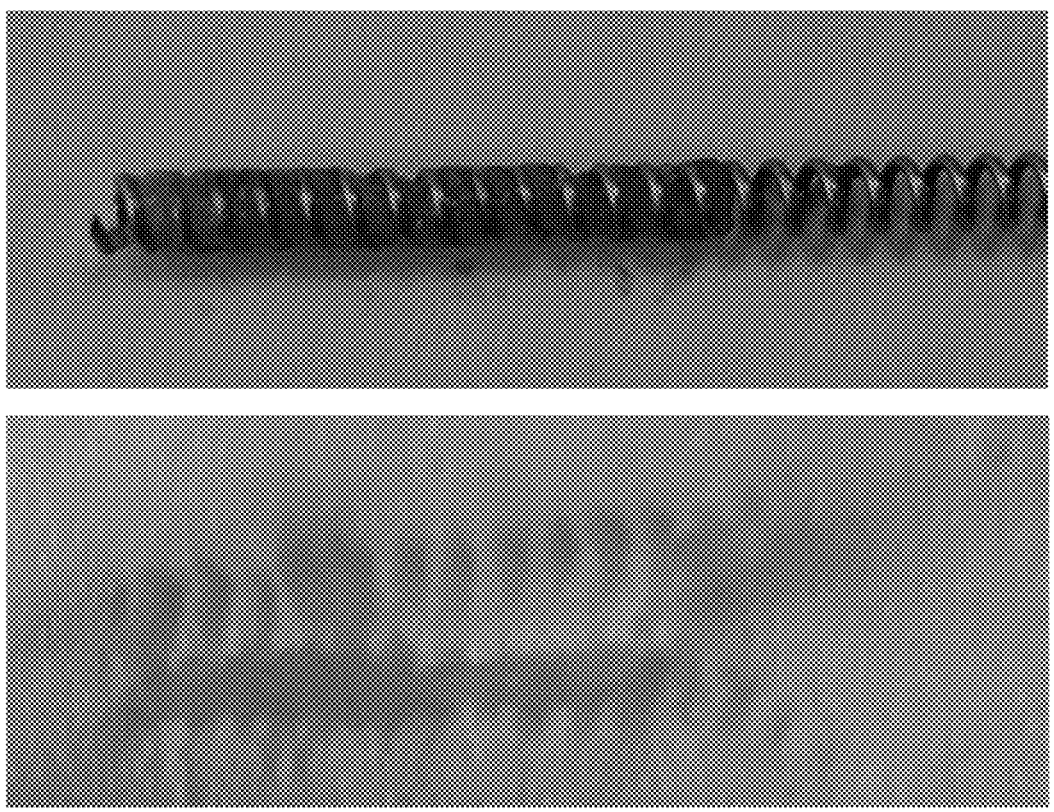
FIG. 31 is a diagram showing the effect of sampling of the spiral soft tissue biopsy needle of example 6.
Figure 32:
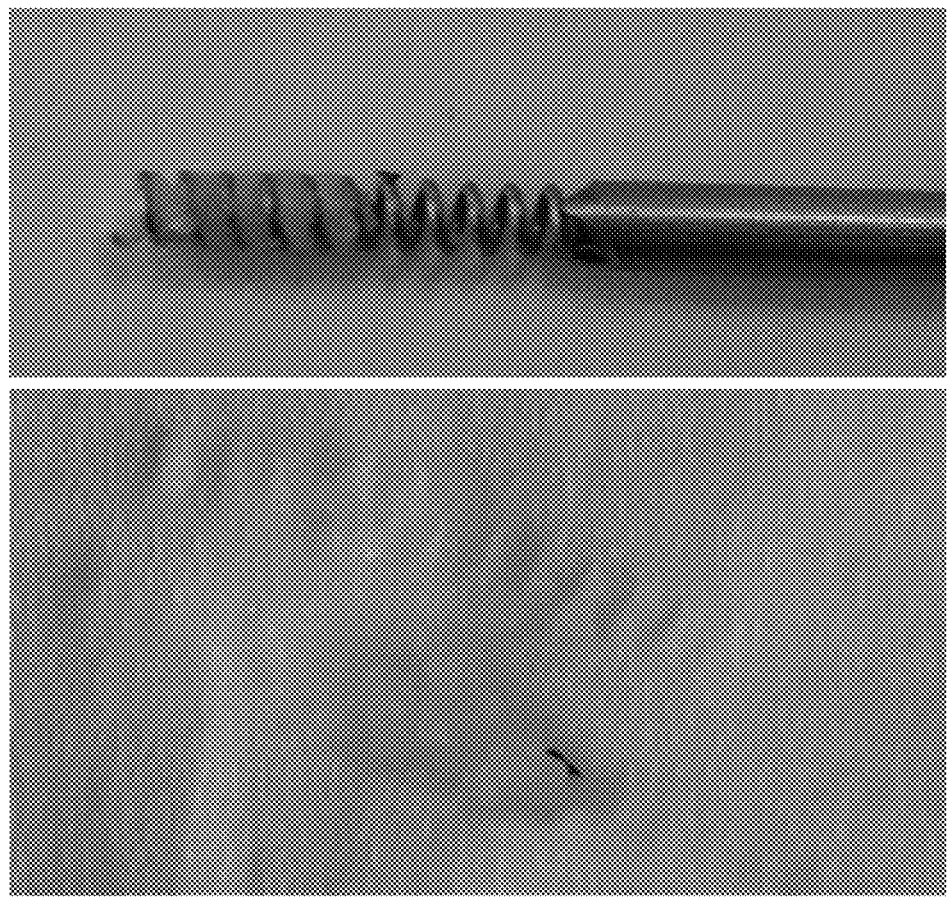
FIG. 32 is a diagram showing the effect of sampling of the spiral soft tissue biopsy needle of example 7.

The sampling effect of the present example is shown in FIG. 31, and it can be seen that the sample obtained has good integrity and continuity, which provides a good stock sample for further analysis such as sample slicing, and localization analysis, etc.

Example 7

The spiral soft tissue biopsy needle of the present example can take samples from different tissues, a process of using which for sampling an adipose tissue comprises the steps of:

S71, connecting the spiral needle rod 21 with the cutting needle rod 22 and fixedly connecting the spiral needle rod fixture 214 with the fixed module 5;

S72, connecting the fixed module 5 with the hand shank 3 fixedly;

S73, adjusting the sampling length by adjusting the length of the spring spiral rod 211 extending out of the cutting needle rod 22, wherein the diameter of the spring spiral tube 211 is selected to be 6 mm, quantitative sampling can be achieved by the diameter of the spring spiral tube 211 and its length of extending, multiple-point continuous sampling can be achieved by increasing the length of the spring spiral rod 211 extending out of the cutting needle rod 22;

S74, connecting the vacuum device 7 with the first joint 72 and performing vacuuming;

S75, under vacuuming, fixing the puncture needle rod 1 on the hand shank 3 and fixing the puncture needle rod 1 on the hand shank 3 and putting the hand shank 3 to puncture to the sampling site, the blood generated in the process of puncture is drawn from the first joint 72;

S76, removing the puncture needle rod 1 from the hand shank 3 and fixing the sampling needle rod 2 on the hand shank 3;

S77, connecting the vacuum device 7 with the second joint 74 and performing vacuuming;

S78, under vacuuming, rotating the spiral needle rod 21 through the rotary rod 4 into the sampling site and fixing it;

S79, under vacuuming, rotating the cutting needle rod 22 through the rotary rod 4 to cut the side of the samples, where in the process of cutting, the cutting edge 221 is in close contact with the thread of the spring spiral tube 211, generating a shear force to cut the samples regularly;

S710, under vacuuming, rotating the spiral needle rod 21 through the rotary rod 4 to cut the bottom of the samples;

S711, taking out the spiral needle rod 21 and cutting needle rod 22, thereby completing the sampling;

S712, taking out the samples and the sampling needle rod 2 from the hand shank 3 at the same time;

S713, opening the sampling device 8, placing the spring spiral tube 211 on the lower sampling groove 84 and closing the sampling device 8;

S714, rotating the spring spiral tube 211 in a reverse direction to separate it from the sampling device 8;

S715, opening the sampling device 8 and taking out the samples.

S716, pushing an absorbent gelatin into the sampling site through the push rod 6, where after taking out the push rod 6 and the sampling outer tube 32, the tissue of the sampling site can automatically close the absorbent gelatin inside the sampling wounds, which is conducive to the recovery of sampling wounds.

The sampling effect of the present example is shown in FIG. 31, and it can be seen that the sample obtained has good integrity and continuity, which provides a good stock sample for further analysis such as sample slicing, and localization analysis, etc.

Figure 16:
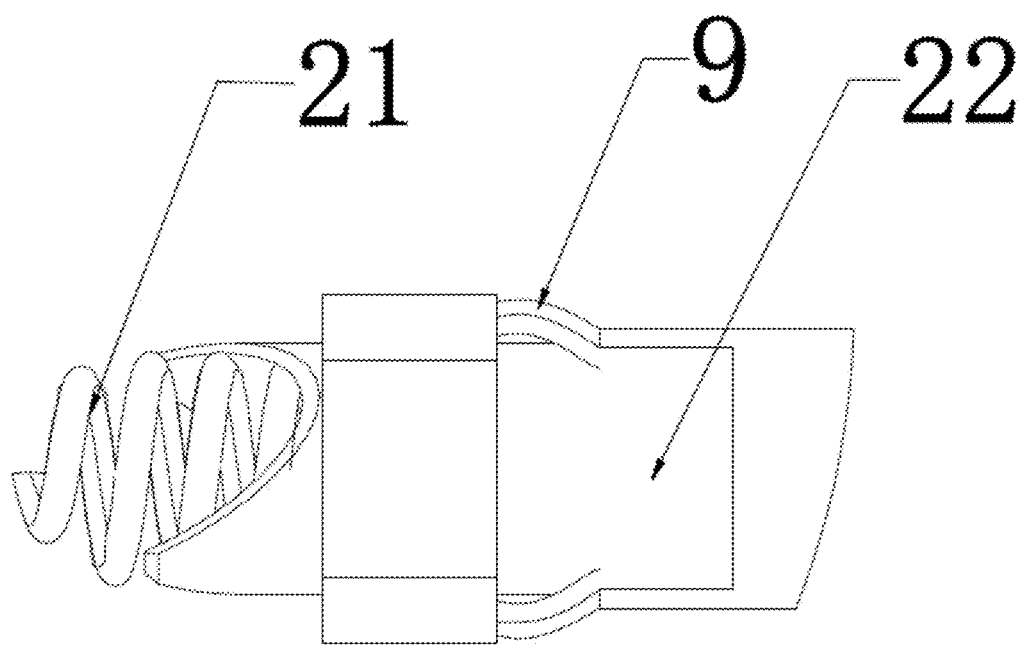
FIG. 16 is the front view of the end cutter of a spiral soft tissue biopsy needle.
Figure 17:
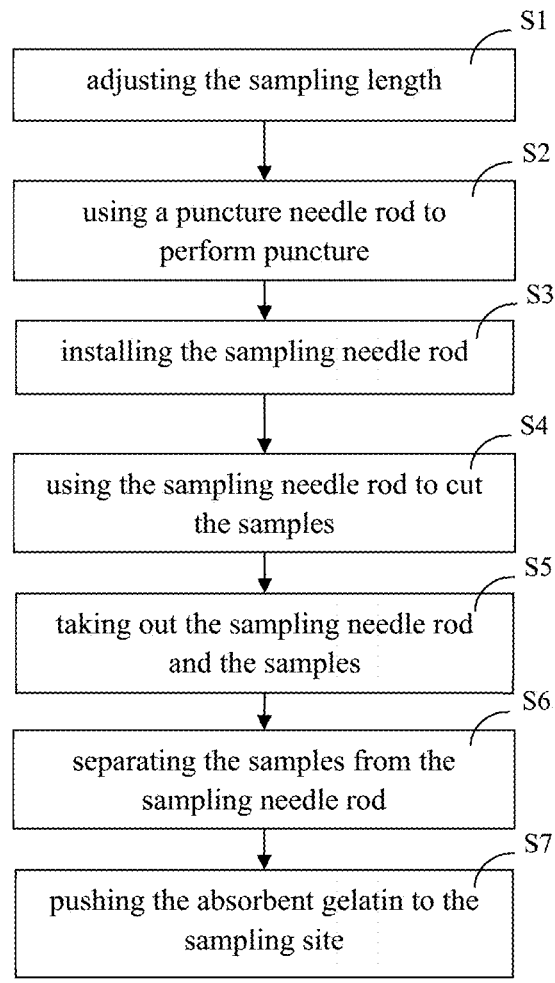
FIG. 17 is a flow chart of a method of using a spiral soft tissue biopsy needle.
Figure 18:
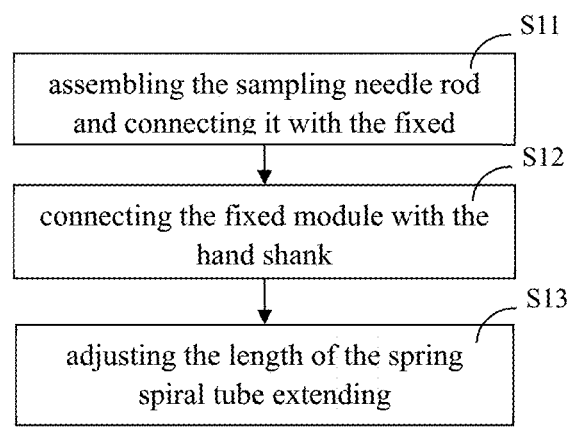
FIG. 18 is a flow chart of step S1 of a method of using a spiral soft tissue biopsy needle.
Figure 19:
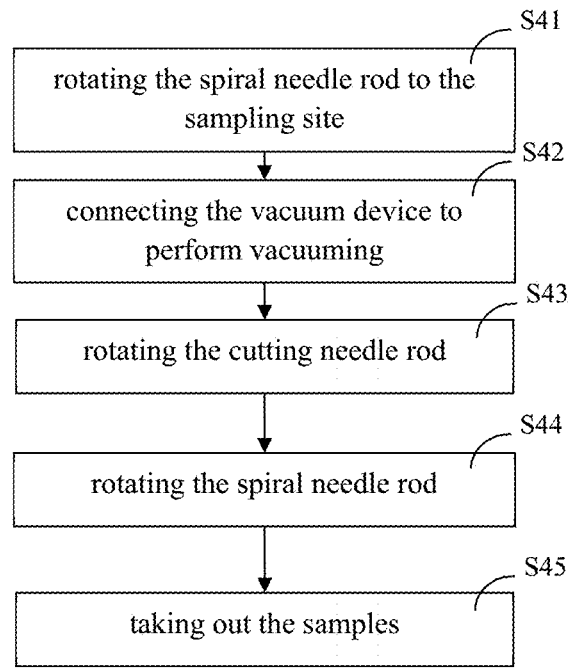
FIG. 19 a flow chart of step S4 of a method of using a spiral soft tissue biopsy needle.
Figure 20:
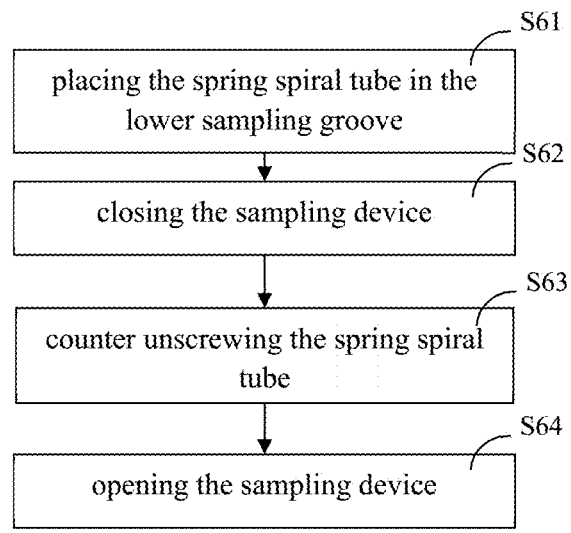
FIG. 20 is a flow chart of step S6 of a method of using a spiral soft tissue biopsy needle.

To achieve taking out small tumors or using as one of minimally invasive surgical instruments, the present invention provides a spiral soft tissue biopsy needle, as shown in FIG. 6, comprising:

a hand shank 3, as shown in FIG. 7, it comprises a handle 31 which is provided in the middle with a through hole for the puncture needle rod 1 or sampling needle rod 2 to go through, the front end of the handle 31 is provided with a hollow sampling outer tube 32 for directional movement of the puncture needle rod 1 or the sampling needle rod 2, a first positioning block 33 is positioned outside the sampling outer tube 33, a fixed groove 34 for fixing the puncture needle rod 1 or the sampling needle rod 2 is arranged on the rear end of the handle 31, and the fixed groove 34 is provided with two steps for fixing the spiral needle rod 21 and the cutting needle rod 22, respectively.

a puncture needle rod 1, which further comprises a puncture needle 11 and a puncture needle rod fixture 12 attached to the tail of the puncture needle 11, the outer diameter of the puncture needle 11 is equal to the inner diameter of the sampling outer tube 32. An assembly of the puncture needle 11 and the hand shank 3 is shown in FIG. 8.

a sampling needle rod 2, which comprises a spiral needle rod 21 for fixing the sampling site and a cutting needle rod 22 for separating the samples from the sampling site, the spiral needle rod 21 has a hollow structure, the outer diameter of the spiral needle rod 21 is equal to the inner diameter of the sampling outer tube 32, the front end of the spiral needle rod 21 is provided with a spring spiral tube 211, in order to cut the front end surface of the samples to be sampled, a spiral cutting edge 212 is provided at the front end of the spring spiral tube, as shown in FIG. 10, the last thread or the last two threads on the front end of the spring spiral tube 211 has a diameter less than the diameter of the other threads of the spring spiral tube 211. The tail of the spring spiral tube 211 is fixedly connected with a spiral needle rod outer tube 213 with a hollow structure, the spiral needle rod outer tube 213 has an outer diameter equal to the inner diameter of the cutting needle rod outer tube 222 and equal to the outer diameter of the spring spiral tube 211 tail, the tail of the spiral needle rod outer tube 213 is provided with a spiral needle rod fixture 214 for fixing the spiral needle rod outer tube 213 to the fixed groove 34; a cutting needle rod 22 is arranged on the outer side of the spiral needle rod 21 and the inner surface of the cutting needle rod 22 is in close contact with the outer surface of the spiral needle rod 21, a cutting edge 221 is arranged on the front end of the cutting needle rod 22, an assembly of the spring spiral tube 211 and the cutting edge 221 is shown in FIG. 11, the cutting needle rod 22 also comprises a cutting needle rod outer tube 222 which has a hollow structure and an outer diameter equal to the inner diameter of the sampling outer tube 32, the cutting edge 221 is arranged on the front end of the cutting needle rod outer tube 222 and has two wavy teeth, the teeth is in close contact with the outer surface of the spring spiral tube 211, the tail of the cutting needle rod outer tube 222 is provided with a cutting needle rod fixture 223 for fixing the cutting needle rod outer tube 222 to the fixed groove 34.

a rotary rod 4, which is arranged on the other end of the spiral needle rod fixture 214 and connected with the spiral needle rod fixture 214 through a thread 41, as shown in FIG. 9.

a fixed module 5, which is connected with the fixed groove 34 for positioning the spiral needle rod 21 and the cutting needle rod 22, the fixed module has a U-shaped cross section and is provided at the middle portion with a first through hole 51 for the thread 41 to go through, the spiral needle rod fixture 214 and the cutting needle rod fixture 223 are arranged in the cavity composed of the fixed groove 34 and the fixed module 5, the outer side of the thread 41 on the front end of the rotary rod 4 is provided with a second positioning block 52 for positioning the spiral needle rod 21 and the cutting needle rod 22.

a push rod 6, which comprises a round rod 61, the tail of the round rod 61 is provided with a push rod fixture 62 for positioning the push rod 6, as shown in FIG. 13.

a vacuum device 7, as shown in FIG. 6, where a second through hole 71 connecting with the hollow part of the sampling outer tube 32 is arranged at the upper end of the handle 31, a first joint 72 is arranged on the outer side of the handle 32 at the upper end of the second through hole 71, a third through hole 73 connecting with the rear end of the sampling outer tube 32 is arranged at the middle part of the rotary rod 4, and a second joint 74 is provided at the outer end of the rotary rod 4 at the outer end of the third through hole 73, and the vacuum device 7 is connected with the first joint 72 or the second joint 74.

a sampling device 8, as shown in FIG. 14-15, which comprises an upper sampling shell 81 and a lower sampling shell 83, the upper sampling shell 81 is provided with an upper sampling groove 82 inside, the lower sampling shell 83 is provided with a lower sampling groove 84 inside, the upper sampling groove 82 corresponds to the lower sampling groove 84 in shape and the shape after their closure coincides with the thread shape of the spring spiral tube 211.

an end cutter 9, as shown in FIG. 16, it is arranged on the outer side of the front end of the sampling needle rod 2 and is made of a memory alloy, and the end cutter 9 comprises at least three arc-shaped end cutter blades.

Figure 27:
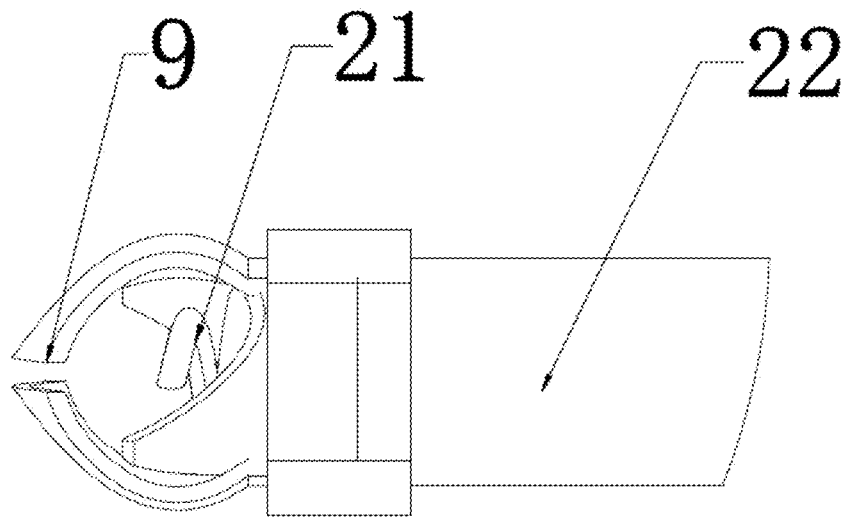
FIG. 27 is a schematic diagram of using the end cutter of a spiral soft tissue biopsy needle.

A process of sampling large samples and resecting small tumors as a whole using the spiral soft tissue biopsy needle according to the present invention comprises the following steps:

S01, adjusting the length of the spring spiral rod 21 extension according to the sampling site;

S02, fixing the puncture needle rod 1 on the hand shank 3 and putting the hand shank 3 to puncture to the sampling site;

S03, removing the puncture needle rod 1 from the hand shank 3 and fixing the sampling needle rod 2 on the hand shank 3;

S04, rotating the sampling needle rod 2 to the sampling site and fixing it, and cutting the sample through the spiral needle rod 21 and cutting needle rod 22;

S041, rotating the spiral needle rod 21 through the rotary rod 4 into the sampling site and fixing it;

S042, connecting the vacuum device 7 with the first joint 72 and performing vacuuming;

S043, rotating the cutting needle rod 22 through the rotary rod 4 to cut the side of the samples;

S044, rotating the spiral needle rod 21 through the rotary rod 4 to cut the bottom of the samples;

S045, taking out the spiral needle rod 21 and cutting needle rod 22, thereby completing the sampling;

S05, taking out the samples and the sampling needle rod 2 from the hand shank 3 at the same time, and allowing the end cutter 9 to cut the end face of the sample inner side during the taking out process, as shown in FIG. 27;

S06, separating the sample from the sampling needle rod 2; comprising

S061, opening the sampling device 8 and placing the spring spiral tube 211 on the lower sampling groove 84;

S062, closing the sampling device 8;

S063, rotating the spring spiral tube 211 in a reverse direction to separate it from the sampling device 8;

S064, opening the sampling device 8 and taking out the samples;

S07, pushing an absorbent gelatin into the sampling site through a push rod 6.

Example 8

The spiral soft tissue biopsy needle of the present example can achieve sampling of small tumors as a whole, comprising the steps of:

S81, connecting the spiral needle rod 21 with the cutting needle rod 22 and fixedly connecting the spiral needle rod fixture 214 with the fixed module 5;

S82, connecting the fixed module 5 with the hand shank 3 fixedly;

S83, adjusting the sampling length by adjusting the length of the spring spiral rod 211 extending out of the cutting needle rod 22, wherein the diameter of the spring spiral tube 211 is selected to be 3 mm;

S84, connecting the vacuum device 7 with the first joint 72 and performing vacuuming;

S85, under vacuuming, fixing the puncture needle rod 1 on the hand shank 3 and fixing the puncture needle rod 1 on the hand shank 3 and putting the hand shank 3 to puncture to the sampling site, the blood generated in the process of puncture is drawn from the first joint 72;

S86, removing the puncture needle rod 1 from the hand shank 3 and fixing the sampling needle rod 2 on the hand shank 3;

S87, connecting the vacuum device 7 with the second joint 74 and performing vacuuming;

S88, under vacuuming, rotating the spiral needle rod 21 through the rotary rod 4 into the sampling site and fixing it;

S89, under vacuuming, rotating the cutting needle rod 22 through the rotary rod 4 to cut the side of the sample, where in the process of cutting, the cutting edge 221 is in close contact with the thread of the spring spiral tube 211, which forms a shear force to cut the samples regularly;

S810, under vacuuming, rotating the spiral needle rod 21 through the rotary rod 4 to cut the bottom of the samples;

S811, taking out the spiral needle rod 21 and cutting needle rod 22 and allowing the end cutter 9 to cut the end face of inner side of the samples to complete the sampling, wherein, the end cutter 9 is made of memory alloy, which can automatically close in the process of taking out the spiral needle rod 21 and cutting needle rod 22 and therefore realize the cutting;

S812, pushing an absorbent gelatin into the sampling site.

The present example can realize the whole removal of the small tumor in the case of small wound surface and can replace the minimally invasive surgery to treat the patients, after taking out the push rod 6 and the sampling outer tube 32, the tissue of the sampling site can automatically close the absorbent gelatin inside the wound caused by the sampling, which helps the recovery of wound.

Example 9

The spiral soft tissue biopsy needle of the present example can be used as medical device for minimally invasive surgery and can take out the hyperplastic bone, a process of using such biopsy needle comprising the steps of:

S91, connecting the spiral needle rod 21 with the cutting needle rod 22 and fixedly connecting the spiral needle rod fixture 214 with the fixed module 5;

S92, connecting the fixed module 5 with the hand shank 3 fixedly;

S93, adjusting the sampling length by adjusting the length of the spring spiral rod 211 extending out of the cutting needle rod 22, wherein the diameter of the spring spiral tube 211 is selected to be 3 mm;

S94, connecting the vacuum device 7 with the first joint 72 and performing vacuuming;

S95, under vacuuming, fixing the puncture needle rod 1 on the hand shank 3 and fixing the puncture needle rod 1 on the hand shank 3 and putting the hand shank 3 to puncture to the sampling site, the blood generated in the process of puncture is drawn from the first joint 72;

S96, removing the puncture needle rod 1 from the hand shank 3 and fixing the sampling needle rod 2 on the hand shank 3;

S97, connecting the vacuum device 7 with the second joint 74 and performing vacuuming;

S98, under vacuuming, rotating the spiral needle rod 21 through the rotary rod 4 into the sampling site and fixing it;

S99, under vacuuming, rotating the cutting needle rod 22 through the rotary rod 4 to cut the side of the sample, wherein, in the process of cutting, the cutting edge 221 is in close contact with the thread of the spring spiral tube 211, which forms a shear force to cut the samples regularly;

S910, under vacuuming, rotating the spiral needle rod 21 through the rotary rod 4 to cut the bottom of the samples;

S911, taking out the spiral needle rod 21 and cutting needle rod 22 and allowing the end cutter 9 to cut the end face of inner side of the samples to complete the sampling, wherein, the end cutter 9 is made of memory alloy, which can automatically close in the process of taking out the spiral needle rod 21 and cutting needle rod 22 and therefore realize the cutting;

S912, pushing an absorbent gelatin into the sampling site, wherein, after taking out the push rod 6 and the sampling outer tube 32, the tissue of the sampling site can automatically close the absorbent gelatin inside the wound caused by the sampling, which is conducive to the recovery of sampling wound.

The present example can achieve removing bone hyperplasia materials with minimal trauma, thus can simplify the process of bone hyperplasia surgery, reduce the risk and difficulty of surgery, and helps rapid recovery of patient.

The foregoing description is intended to be illustrative only and not limited to the present invention, and it will be understood by those skilled in the art that various changes, modifications and equivalents made therein without departing from the spirit and scope of the invention as defined by the appended claims, will fall within the scope of the present invention.

What is claimed is:

1. A spiral soft tissue biopsy needle, comprising a puncture needle rod (1), a sampling needle rod (2), and a hand shank (3) for fixing the puncture needle rod (1) and the sampling needle rod (2), wherein the sampling needle rod (2) comprises a spiral needle rod (21) for fixing the sampling site and a cutting needle rod (22) for separating the sample from the sampling site, the spiral needle rod (21) has a hollow structure, the cutting needle rod (22) is arranged on an outer side of the spiral needle rod (21) and an inner surface of the cutting needle rod (22) is in close contact with an outer surface of the spiral needle rod (21), a front end of the spiral needle rod (21) is provided with a spring spiral tube (211), and an front end of the cutting needle rod (22) is provided with a cutting edge (221) and wherein the hand shank (3) comprises a handle (31) which is provided in a middle portion a through hole for the puncture needle rod (1) or sampling needle rod (2) to go through, a front end of the handle (31) is provided with a hollow sampling outer tube (32) for directional movement of the puncture needle rod (1) or the sampling needle rod (2), an outer side of the sampling outer tube (32) is provided with a first positioning block (33), a rear end of the handle (31) is provided with a fixation groove (34) for fixing the puncture needle rod (1) or the sampling needle rod (2), and the fixation groove (34) is provided with two steps for fixing the spiral needle rod (21) and the cutting needle rod (22), respectively.

2. The spiral soft tissue biopsy needle according to claim 1, wherein a front end of the spring spiral tube (211) is provided with a spiral cutting edge (212).

3. The spiral soft tissue biopsy needle according to claim 1, wherein the last thread or the last two threads on a front end of the spring spiral tube (211) has a diameter less than a diameter of other threads of the spring spiral tube (211).

4. The spiral soft tissue biopsy needle according to claim 1, wherein the puncture needle rod (1) further includes a puncture needle (11) and a puncture needle rod fixture (12) attached to a tail of the puncture needle (11), an outer diameter of the puncture needle is equal to an inner diameter of the sampling outer tube (32).

5. The spiral soft tissue biopsy needle according to claim 4, wherein the spiral needle rod (21) further comprises a spiral needle rod outer tube (213) fixedly connected to a tail end of the spring spiral tube (211), the spiral needle rod outer tube (213) has a hollow structure and has an outer diameter equal to an inner diameter of the cutting needle rod (22) and equal to an outer diameter of the tail end of the spring spiral tube (211), a tail end of the spiral needle rod outer tube (213) is provided with a spiral needle rod fixture (214) for fixing the spiral needle rod outer tube (213) to the fixation groove (34).

6. The spiral soft tissue biopsy needle according to claim 5, wherein the cutting needle rod (22) comprises an cutting needle rod outer tube (222) with a hollow structure and an outer diameter equal to the inner diameter of the sampling outer tube (32), the cutting edge (221) is arranged on an front end of the cutting needle rod outer tube (222), and a cutting needle rod fixture (223) for fixing the cutting needle rod outer tube (222) to the fixation groove (34) is provided at a tail end of the cutting needle rod outer tube (222).

7. The spiral soft tissue biopsy needle according to claim 6, wherein the cutting edge (221) has at least two teeth which are in contact with an outer surface of the spring spiral tube (211).

8. The spiral soft tissue biopsy needle according to claim 7, wherein a rear end of the spiral needle rod (21) is provided with a rotary rod (4) for rotating the spiral needle rod (21), and the rotary rod (4) and the spiral needle rod fixture (214) are connected through a thread (41).

9. The spiral soft tissue biopsy needle according to claim 8, wherein the fixation groove (34) is provided with a fixed module (5) for positioning the spiral needle rod (21) and the cutting needle rod (22), the fixed module (5) has a U-shaped cross section and is provided in a middle portion with a first through hole (5) for the thread (41) to go through, the spiral needle rod fixture (214) and the cutting needle rod fixture (223) are arranged in a cavity composed of the fixation groove (34) and the fixed module (5), an outer side of the thread (41) on a front end of the rotary rod (4) is provided with a second positioning block (52) for positioning the spiral needle rod (21) and the cutting needle rod (22).

10. The spiral soft tissue biopsy needle according to claim 9, further comprising a vacuum device (7), a second through hole (71) connecting with a hollow part of the sampling outer tube (32) is arranged at the upper end of the handle (31), a first joint (72) is arranged on the outer side of the handle (31) at an upper end of the second through hole (71), a third through hole (73) connecting with a rear end of the sampling outer tube (32) is arranged in a middle portion of the rotary rod (4), and a second joint (74) is provided at an outer end of the rotary rod (4) at an outer end of the third through hole (73), and the vacuum device (7) is connected with the first joint (72) or the second joint (74).

* * * * *